US006440697B1

(12) United States Patent
Venezia et al.

(10) Patent No.: US 6,440,697 B1
(45) Date of Patent: Aug. 27, 2002

(54) RING FINGER PROTEIN ZAPOP3

(75) Inventors: Domenick Venezia; Angelika Grossmann, both of Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/434,408

(22) Filed: Nov. 4, 1999

Related U.S. Application Data

(60) Provisional application No. 60/108,258, filed on Nov. 12, 1998.

(51) Int. Cl.[7] .......................... C12P 21/06; C07H 5/04; C07H 5/00; C07H 19/00; C07H 21/00
(52) U.S. Cl. ...................... 435/69.1; 435/325; 536/18.7; 536/22.1; 536/23.1; 536/23.5; 536/24.3; 536/24.31; 536/24.33
(58) Field of Search .......................... 536/23.1, 1, 18.7, 536/22.1, 23.5, 24.3, 24.31, 24.33; 435/69.1, 325

(56) References Cited

PUBLICATIONS

Jensen, D.E. et al., *Oncogene* 16:1097–1112, 1998.
Wang, H. et al., *Oncogene* 15:143–157, 1997.
Buchanan, S. and Gay, N., *Prog. Biophys. Molec. Biol.* 65:1–44, 1996.
Brzovic, P.S. et al., *J. Biol. Chem.* 273:7795–7799, 1998.
Public EST 1993: EST33455.
Public EST 1993: EST33464.
Public EST 1993: EST33469.
Public EST 1993: EST33465.
Public EST 1993: EST33467.
Public EST 1994: EST73262.
Public EST 1995: EST224021.
Incyte, Inc. clone 1995: INC377292.
Incyte, Inc. clone 1995: INC728570.
Incyte, Inc. clone 1996: INC835464.
Incyte, Inc. clone 1996: INC837927.
Incyte, Inc. clone 1996: INC923770.
Incyte, Inc. clone 1996: INC854778.
Incyte, Inc. clone 1996: INC1253675.
Incyte, Inc. clone 1996: LIN377292R1.
Incyte, Inc. clone 1996: INC1538230.
Incyte, Inc. clone 1996: INC1562894.
Public EST 1996: EST595103.
Incyte, Inc. clone 1996: INC1943491.
Incyte, Inc. clone 1996: INC1960343.
Incyte, Inc. clone 1996: INC1962629.
Incyte, Inc. clone 1996: INC2119982.
Incyte, Inc. clone 1996: INC2170848.
Incyte, Inc. clone 1996: INC2292581.
Incyte, Inc. clone 1997: INC2589627.
Incyte, Inc. clone 1997: INC2616656.
Public EST 1997: EST963618.
Incyte, Inc. clone 1997: INC2750559.
Incyte, Inc. clone 1997: INC3015287.
TIGR Tentative Human Consensus 1997: THC_T12647.
TIGR Tentative Human Consensus 1997: THC_T12650.
TIGR Tentative Human Consensus 1997: THC_T12652.
TIGR Tentative Human Consensus 1997: THC_T12648.
TIGR Tentative Human Consensus 1997: THC_R53956.
TIGR Tentative Human Consensus 1997: THC_T12638.
TIGR Tentative Human Consensus 1997: THC_EST24932.
Incyte, Inc. clone 1997: INC2413163.
Incyte, Inc. clone 1997: INC3372223.
Incyte, Inc. clone 1997: INC3366339.
Incyte, Inc. clone 1997: INC3614483.
Incyte, Inc. clone 1997: INC3486312.
Incyte, Inc. clone 1997: INC3800831.
Incyte, Inc. clone 1997: INC4017623.
Incyte, Inc. clone 1998: INC4046956.
Public EST 1998: EST1499151.
Incyte, Inc. clone 1998: INC4338012.
Incyte, Inc. clone 1998: INC3385419.
Incyte, Inc. clone 1998: INC1388932.
ACE Assembly, ACE_EST33465, 1997.
ACE Assembly, ACE_LISF2056020 1998.
ACE Assembly, ACE_LPIF2014184, 1997.
ACE Assembly, ACE_LKFG2005184, 1997.
ACE Assembly, ACE_LISF2019884, 1997.
Incyte, Inc. Library 1995: NEUTFMT01.
Incyte, Inc. Library 1995: SYNOOAT01.
Incyte, Inc. Library 1996: PROSNOT07.
Incyte, Inc. Library 1996: RATRNOT02.
Incyte, Inc. Library 1996: NGANNOT01.
Incyte, Inc. Library 1996: LUNGFET03.
Incyte, Inc. Library 1996: SYNTTUT01.
Incyte, Inc. Library 1996: SPLNNOT04.
Incyte, Inc. Library 1996: HIPONOT01.
Incyte, Inc. Library 1996: BRSTNOT04.
Incyte, Inc. Library 1996: BRSTTUT02.
Incyte, Inc. Library 1996: ENDCNOT03.
Incyte, Inc. Library 1996: BRAINON01.
Incyte, Inc. Library 1997: LUNGNOT22.
Incyte, Inc. Library 1997: GBLANOT01.
Incyte, Inc. Library 1997: THP1AZS08.
Incyte, Inc. Library 1997: MUSCNOT07.
Incyte, Inc. Library 1997: BSTMNON02.
Incyte, Inc. Library 1997: CONNTUT05.
Incyte, Inc. Library 1997: CONNTUT04.
Incyte, Inc. Library 1997: EPIPNOT01.
Incyte, Inc. Library 1997: EPIGNOT01.
Incyte, Inc. Library 1997: SPLNNOT12.
Incyte, Inc. Library 1997: BRAXNOT01.
Incyte, Inc. Library 1998: LUNGNOT35.
Incyte, Inc. Library 1998: BRAUNOT02.
Incyte, Inc. Library 1998: ESOGNOT04.
Incyte, Inc. Library 1998: EOSINOT01.

*Primary Examiner*—Anthony C. Caputa
*Assistant Examiner*—Alana M. Harris
(74) *Attorney, Agent, or Firm*—Jennifer K. Johnson

(57) ABSTRACT

The present invention relates to polynucleotide and polypeptide molecules for zapop3, a novel human member of the RING finger protein family. The polypeptides, and polynucleotides encoding them, may be used for detecting human chromosomal abnormalities. The present invention also includes antibodies to the zapop3 polypeptides.

4 Claims, 17 Drawing Sheets

| | | | | |
|---|---|---|---|---|
| 84 | 0.15 | | E K | == |
| 85 | 0.60 | | E V | ====== |
| 86 | 0.93 | | E L | ========= |
| 87 | 1.73 | | C D | ================= |
| 88 | 0.93 | | C L | ========= |
| 89 | 1.17 | | C H | =========== |
| 90 | 0.67 | | C D | ======= |
| 91 | -0.13 | = | C N | |
| 92 | -0.17 | == | C Q | |
| 93 | -0.17 | == | C L | |
| 94 | 0.63 | | C T | ====== |
| 95 | 0.40 | | C A | ==== |
| 96 | 0.23 | | C L | == |
| 97 | 1.03 | | C P | ========== |
| 98 | 0.73 | | C D | ======= |
| 99 | 0.17 | | C D | == |
| 100 | -0.33 | === | C L | |
| 101 | -0.33 | === | C G | |
| 102 | 0.33 | | C Q | === |
| 103 | -0.47 | ===== | C L | |
| 104 | -0.47 | ===== | C T | |
| 105 | -0.37 | ==== | C A | |
| 106 | -0.67 | ======= | E L | |
| 107 | 0.13 | | E Q | = |
| 108 | -0.45 | ==== | E V | |
| 109 | -0.12 | = | E L | |
| 110 | 0.68 | | E N | ======= |
| 111 | 0.35 | | H V | ==== |
| 112 | 0.08 | | H E | = |
| 113 | 0.08 | | H R | = |
| 114 | -0.13 | = | H N | |
| 115 | -0.17 | == | H Q | |
| 116 | -0.75 | ======== | H L | |
| 117 | -0.53 | ===== | H M | |
| 118 | -0.38 | ==== | H Q | |
| 119 | -1.05 | =========== | C L | |
| 120 | -0.72 | ======= | C P | |
| 121 | -1.02 | ========== | C R | |
| 122 | -1.00 | ========== | C S | |
| 123 | -0.42 | ==== | C I | |
| 124 | -0.30 | === | C G | |
| 125 | 0.37 | | C N | ==== |
| 126 | 0.27 | | C L | === |

| | | | |
|---|---|---|---|
| 213 | 0.48 | | C Y ===== |
| 214 | 0.15 | | C P == |
| 215 | -0.15 | = | C P |
| 216 | -0.15 | = | C S |
| 217 | -0.48 | ===== | C Q |
| 218 | -1.28 | ============ | E Y |
| 219 | -0.82 | ======== | E L |
| 220 | -0.02 | | E L |
| 221 | 0.78 | | E P ======== |
| 222 | 0.62 | | E I ====== |
| 223 | 0.62 | | C L ====== |
| 224 | 1.42 | | C E ============== |
| 225 | 0.95 | | C Q ========= |
| 226 | 0.37 | | C D ==== |
| 227 | -0.22 | == | C G |
| 228 | 0.45 | | C I ===== |
| 229 | 0.78 | | C E ======== |
| 230 | 0.28 | | C N === |
| 231 | 0.75 | | C S ======== |
| 232 | 0.67 | | C R ======= |
| 233 | 0.75 | | C D ======== |
| 234 | 0.18 | | C S == |
| 235 | 0.77 | | C P ======== |
| 236 | 0.68 | | C D ======= |
| 237 | -0.20 | == | C G |
| 238 | -0.12 | = | C P |
| 239 | -0.20 | == | C T |
| 240 | 0.37 | | C D ==== |
| 241 | 0.37 | | C R ==== |
| 242 | 0.15 | | C F == |
| 243 | 1.03 | | C S ========== |
| 244 | 0.87 | | H R ========= |
| 245 | 1.45 | | H E ============== |
| 246 | 0.98 | | H E ========== |
| 247 | 0.40 | | H L ==== |
| 248 | 0.32 | | H E === |
| 249 | -0.27 | === | H W |
| 250 | 0.48 | | H Q ===== |
| 251 | 0.42 | | H N ==== |
| 252 | 0.88 | | C R ========= |
| 253 | 1.02 | | C F ========== |
| 254 | 1.32 | | C S ============ |
| 255 | 1.45 | | C D ============== |

FIG. 1F

| | | | |
|---|---|---|---|
| 256 | 1.45 | C y | ============== |
| 257 | 1.52 | C E | ============== |
| 258 | 1.07 | H K | ========== |
| 259 | 0.45 | H R | ===== |
| 260 | 0.23 | H K | == |
| 261 | 0.68 | H E | ======= |
| 262 | 0.23 | H Q | == |
| 263 | -0.57 | ====== H K | |
| 264 | -0.12 | = H M | |
| 265 | 0.07 | H L | = |
| 266 | 0.87 | H E | ========= |
| 267 | 0.28 | H K | === |
| 268 | 0.15 | H L | == |
| 269 | 0.15 | H E | == |
| 270 | 0.15 | H F | == |
| 271 | 0.23 | H E | == |
| 272 | -0.43 | ==== H R | |
| 273 | 0.15 | H R | == |
| 274 | 0.15 | H L | == |
| 275 | 0.95 | H E | ========== |
| 276 | 1.35 | H L | ============= |
| 277 | 1.58 | H G | ============== |
| 278 | 2.25 | H Q | ====================== |
| 279 | 1.45 | H R | ============= |
| 280 | 1.23 | H E | ============ |
| 281 | 1.23 | H h | ============ |
| 282 | 0.83 | H T | ======== |
| 283 | 0.82 | H Q | ======== |
| 284 | 0.23 | H L | == |
| 285 | 0.45 | H L | ==== |
| 286 | 1.25 | H Q | ============ |
| 287 | 0.80 | H Q | ======== |
| 288 | 0.80 | C S | ======== |
| 289 | 1.38 | C S | ============ |
| 290 | 1.05 | C S | ========== |
| 291 | 0.83 | C Q | ======== |
| 292 | 0.83 | C K | ======== |
| 293 | 0.72 | H D | ======= |
| 294 | -0.08 | = H E | |
| 295 | -0.53 | ===== H I | |
| 296 | 0.38 | H L | ==== |
| 297 | 1.18 | H Q | =========== |
| 298 | 1.18 | H T | =========== |

FIG. 1G

| | | | |
|---|---|---|---|
| 299 | 1.17 | H V | ============ |
| 300 | 1.38 | H K | ============= |
| 301 | 1.03 | H E | ========== |
| 302 | 1.03 | H E | ========== |
| 303 | 1.03 | H Q | ========== |
| 304 | 0.37 | H S | ==== |
| 305 | 0.15 | H R | == |
| 306 | 0.15 | H L | = |
| 307 | 0.95 | H E | ========== |
| 308 | 1.35 | H Q | ============= |
| 309 | 1.35 | C G | ============= |
| 310 | 1.43 | C L | ============== |
| 311 | 2.23 | C S | ====================== |
| 312 | 2.02 | C E | =================== |
| 313 | 1.55 | C h | =============== |
| 314 | 0.65 | H Q | ======= |
| 315 | 0.65 | H R | ======= |
| 316 | 0.65 | H H | ======= |
| 317 | 0.65 | H L | ======= |
| 318 | 0.87 | H N | ========= |
| 319 | 0.53 | H A | ===== |
| 320 | 1.03 | H E | ========== |
| 321 | 1.03 | H R | ========== |
| 322 | 1.62 | H Q | ================ |
| 323 | 0.82 | H R | ======== |
| 324 | 0.95 | H L | ========== |
| 325 | 1.75 | H Q | ================= |
| 326 | 1.18 | H E | ============ |
| 327 | 1.18 | H Q | ============ |
| 328 | 1.18 | H L | ============ |
| 329 | 1.52 | H K | =============== |
| 330 | 1.05 | H Q | ========== |
| 331 | 0.47 | H T | ===== |
| 332 | 0.45 | C E | ==== |
| 333 | -0.13 | = C Q | |
| 334 | -1.05 | ========== C N | |
| 335 | -0.58 | ====== C I | |
| 336 | -0.12 | = C S | |
| 337 | -0.33 | === C S | |
| 338 | -0.55 | ====== C R | |
| 339 | 0.03 | H I | |
| 340 | 0.95 | H Q | ========== |
| 341 | 0.48 | H K | ===== |

| | | | |
|---|---|---|---|
| 514 | -0.20 | == | H L |
| 515 | 0.15 | | H L = |
| 516 | 0.95 | | H Q ========== |
| 517 | 0.50 | | H Q ===== |
| 518 | 0.50 | | H L ===== |
| 519 | 1.30 | | H L ============ |
| 520 | 1.52 | | H K ============== |
| 521 | 1.97 | | H E =================== |
| 522 | 1.97 | | H K =================== |
| 523 | 2.42 | | H Q ======================== |
| 524 | 1.62 | | H Q ================ |
| 525 | 1.03 | | H R ========== |
| 526 | 1.62 | | H E ================ |
| 527 | 0.70 | | H E ======= |
| 528 | -0.10 | = | H E |
| 529 | -0.67 | ======= | H L |
| 530 | 0.13 | | H R = |
| 531 | -0.08 | = | H E |
| 532 | -0.08 | = | H I |
| 533 | 0.33 | | H L === |
| 534 | 0.68 | | H T ======= |
| 535 | 0.67 | | H E ======= |
| 536 | 0.67 | | H L ======= |
| 537 | 0.90 | | H E ========= |
| 538 | 0.32 | | H A === |
| 539 | 0.82 | | H K ======== |
| 540 | 1.27 | | H S ============ |
| 541 | 1.38 | | H E ============= |
| 542 | 0.92 | | H T ========= |
| 543 | 0.73 | | H R ======= |
| 544 | 0.52 | | H Q ===== |
| 545 | -0.40 | ==== | H E |
| 546 | -0.40 | ==== | H N |
| 547 | -0.40 | ==== | E Y |
| 548 | 0.07 | | E W = |
| 549 | 0.23 | | E L == |
| 550 | 0.23 | | E I == |
| 551 | 0.35 | | E Q ==== |
| 552 | -0.12 | = | E Y |
| 553 | 0.35 | | E Q ==== |
| 554 | -0.10 | = | C R |
| 555 | -0.02 | | C L |
| 556 | -0.02 | | C L |

FIG. 1M

| | | | |
|---|---|---|---|
| 557 | 0.20 | | C N == |
| 558 | -0.13 | = | C Q |
| 559 | -0.58 | ====== | C K |
| 560 | -0.93 | ======== | C P |
| 561 | -0.43 | ==== | C L |
| 562 | 0.37 | | C S ==== |
| 563 | 0.95 | | H L ========== |
| 564 | 1.08 | | H K ========== |
| 565 | 0.47 | | H L ===== |
| 566 | 1.27 | | H Q ============ |
| 567 | 0.68 | | H E ======= |
| 568 | 0.68 | | H E ======= |
| 569 | -0.12 | = | H G |
| 570 | -0.25 | === | H M |
| 571 | 0.32 | | H E === |
| 572 | -0.48 | ===== | H R |
| 573 | -0.70 | ======= | H Q |
| 574 | -0.70 | ======= | H L |
| 575 | 0.10 | | H V = |
| 576 | 0.10 | | H A = |
| 577 | 0.02 | | H L |
| 578 | 0.32 | | H L === |
| 579 | 1.12 | | H E =========== |
| 580 | 1.12 | | H E =========== |
| 581 | 0.65 | | H L ======= |
| 582 | 0.65 | | H S ======= |
| 583 | 0.73 | | H A ======= |
| 584 | 0.32 | | H E === |
| 585 | -0.57 | ====== | H H |
| 586 | -1.07 | ========== | C Y |
| 587 | -0.60 | ====== | E L |
| 588 | 0.20 | | E P == |
| 589 | 0.12 | | E I = |
| 590 | 0.23 | | E F == |
| 591 | 0.53 | | E A ===== |
| 592 | 0.23 | | E H == |
| 593 | 0.23 | | E H == |
| 594 | -0.57 | ====== | H R |
| 595 | -0.78 | ======= | H L |
| 596 | -0.57 | ====== | H S |
| 597 | 0.02 | | H L |
| 598 | -0.25 | === | H D |
| 599 | -0.83 | ======== | H L |

```
686  -1.45    ============ H I
687  -0.53        ===== E F
688  -0.45         ==== E L
689  -0.37         ==== E N
690  -0.62        ====== E C
691  -0.62        ====== E G
692   0.05              E H =
693   0.05              E V =
694   0.13              E C =
695   0.13              E C =
696   0.85              E C =========
697   1.07              C Q ===========
698   0.27              C Q ===
699  -0.32           === C C
700  -0.17            == C C
701  -0.17            == C Q
702  -0.67       ====== C P
703  -0.97    ========= C L
704  -0.88     ======== C R
705  -0.88     ======== C T
706  -0.32           === C C
707   0.40              C P ====
708  -0.02              C L
709   0.28              C C ===
710   1.00              H R ==========
711   1.00              H Q ==========
712   0.20              H D ==
713  -0.27           === H I
714  -0.16            == H A
715  -0.02              H Q
716   0.09              H R =
717   0.21              H L ==
718   0.53              E R =====
719   0.00              E I
720   0.00              E Y
721   0.00              C H
722   0.00              X S
723   0.00              X S
         |---------|---------|--------- |---------|---------|---------|
        -3        -2        -1         0         1         2         3
        Hydrophobic                                         Hydrophilic
```

RING FINGER PROTEIN ZAPOP3

REFERENCE TO RELATED APPLICATIONS

This application is related to Provisional Application No. 60/108,258, filed on Nov. 12, 1998. Under 35 U.S.C. §119 (e)(1), this application claims benefit of said Provisional Application.

BACKGROUND OF THE INVENTION

Proper control of the opposing processes of cell proliferation versus terminal differentiation and apoptotic programmed cell death is an important aspect of normal development and homeostasis (Raff, M. C., Cell 86:173–175, 1996), and has been found to be altered in many human diseases. See, for example, Sawyers, C. L. et al., Cell 64:337–350, 1991; Meyaard, L. et al., Science 257:217–219, 1992; Guo, Q. et al., Nature Med. 4:957–962, 1998; Barinaga, M., Science, 273:735–737, 1996; Solary, E. et al., Eur. Respir. J., 9:1293–1305, 1996; Hamet, P. et al., J. Hypertension, 14:S65–S70, 1996; Roy, N. et al., Cell, 80:167–178, 1995; and Ambrosini, G., Nature Med., 8:917–921, 1997. Much progress has been made towards understanding the regulation of this balance. For example, signaling cascades have been elucidated through which extracellular stimuli, such as growth factors, peptide hormones, and cell-cell interactions, control the commitment of precursor cells to specific cell lineages and their subsequent proliferative expansion (Morrison, S. J. et al., Cell 88:287–298, 1997). Further, it has been found that cell cycle exit and terminal differentiation are coupled in most cell types. See, for example, Coppola, J. A. et al., Nature 320:760–763, 1986; Freytag, S. O, Mol. Cell. Biol. 8:1614–1624, 1988; Lee, E. Y. et al., Genes Dev. 8:2008–2021, 1994; Morgenbesser, S. D. et al., Nature 371:72–74, 1994; Casaccia-Bonnefil, P. et al., Genes Dev. 11:2335–2346, 1996; Zacksenhaus, E. et al., Genes Dev. 10:3051–3064, 1996; and Zhang, P. et al., Nature 387:151–158, 1997. Apoptosis also plays an important role in many developmental and homeostatic processes (Raff, M. C., Nature 356:397–400, 1992; Raff, M. C., supra.), and is often coordinately regulated with terminal differentiation (Jacobsen, K. A. et al., Blood 84:2784–2794, 1994; Morgenbesser et al., supra.; Yan, Y. et al., Genes Dev. 11:973–983, 1997; Zacksenhaus et al., supra.). Hence, it appears that the development of individual lineages, tissues, organs, or even entire multicellular organisms is the result of a finely tuned balance between increased cell production due to proliferation, and decreased numbers of cells resulting from terminal differentiation and apoptosis. This balance is most likely regulated coordinately by the convergence of multiple regulatory pathways. The identification of novel members of such networks can provide important insights into both normal cellular processes, as well as the etiology and treatment of human disease states.

Thus, there is a continuing need to discover new proteins that regulate proliferation, differentiation, and apoptotic pathways. The in vivo activities of inducers and inhibitors of these pathways illustrates the enormous clinical potential of, and need for, novel proliferation, differentiation, and apoptotic proteins, their agonists and antagonists. The present invention addresses this need by providing such polypeptides for these and other uses that should be apparent to those skilled in the art from the teachings herein.

SUMMARY OF THE INVENTION

The present invention addresses this need by providing a novel polypeptide and related compositions and methods.

Within one aspect, the present invention provides an isolated polynucleotide that encodes a polypeptide comprising a sequence of amino acid residues that is at least 90% identical to an amino acid sequence as shown in SEQ ID NO:2 from amino acid number 1 (Met), to amino acid number 723 (Ser), wherein the amino acid percent identity is determined using a FASTA program with ktup=1, gap opening penalty=10, gap extension penalty=1, and substitution matrix=BLOSUM62, with other parameters set as default. Within one embodiment the isolated polynucleotide disclosed above, wherein the polynucleotide is selected from the group consisting of: (a) polynucleotide molecules comprising a nucleotide sequence as shown in SEQ ID NO:1 from nucleotide 367 to nucleotide 2535; and (b) polynucleotide molecules complementary to (a). Within another embodiment the isolated polynucleotide disclosed above comprises nucleotide 1 to nucleotide 2169 of SEQ ID NO:3. Within another embodiment the isolated polynucleotide disclosed above comprises a sequence of amino acid residues having an amino acid sequence as shown in SEQ ID NO:2 from amino acid number 1 (Met), to amino acid number 723 (Ser). Within another embodiment the isolated polynucleotide disclosed above consists of an amino acid sequence as shown in SEQ ID NO:2 from amino acid number 1 (Met), to amino acid number 723 (Ser). Within another embodiment the isolated polynucleotide disclosed above further encodes a polypeptide that contains a RING finger domain or at least one LRR motif. Within another embodiment the isolated polynucleotide disclosed above further encodes a polypeptide that contains a RING finger domain and at least one LRR motif.

Within a second aspect, the present invention provides an expression vector comprising the following operably linked elements: a transcription promoter; a DNA segment encoding a zapop3 polypeptide having an amino acid sequence as shown in SEQ ID NO:2 from amino acid number 1 (Met), to amino acid number 723 (Ser); and a transcription terminator, wherein the promoter is operably linked to the DNA segment, and the DNA segment is operably linked to the transcription terminator. Within one embodiment the expression vector disclosed above further comprises a secretory signal sequence operably linked to the DNA segment.

Within a third aspect, the present invention provides a cultured cell into which has been introduced an expression vector as disclosed above, wherein the cell expresses the polypeptide encoded by the DNA segment.

Within a fourth aspect, the present invention provides an isolated polypeptide comprising a sequence of amino acid residues that is at least 90% identical to an amino acid sequence selected from the group consisting of: (a) polypeptide molecules comprising an amino acid sequence as shown in SEQ ID NO:2 from amino acid number 1 (Met), to amino acid number 723 (Ser), wherein the amino acid percent identity is determined using a FASTA program with ktup=1, gap opening penalty=10, gap extension penalty=1, and substitution matrix=BLOSUM62, with other parameters set as default. Within one embodiment, the isolated polypeptide disclosed above comprises a sequence of amino acid residues having an amino acid sequence as shown in SEQ ID NO:2 from amino acid number 1 (Met), to amino acid number 723 (Ser). Within another embodiment, the isolated polypeptide disclosed above consists of amino acid number 1 (Met), to amino acid number 723 (Ser) of SEQ ID NO:2. Within another embodiment, the isolated polypeptide disclosed above further contains a RING finger domain or at least one LRR motif; Within another embodiment, the isolated polypeptide disclosed above further contains a RING finger domain and at least one LRR motif. Within another aspect, the present invention provides a method of producing a zapop3 polypeptide comprising: culturing a cell as disclosed above; and isolating the zapop3 polypeptide produced by the cell.

Within another aspect, the present invention provides a method of producing an antibody to zapop3 polypeptide comprising: inoculating an animal with a polypeptide selected from the group consisting of: (a) a polypeptide consisting of 9 to 723 amino acids, wherein the polypeptide consists of a contiguous sequence of amino acids in SEQ ID NO:2 from amino acid number 1 (Met), to amino acid number 723 (Ser); (b) a polypeptide as disclosed above; (c) a polypeptide consisting of the amino acid sequence of SEQ ID NO:2 from amino acid residue 1 (Met) to amino acid residue 223 (Leu); (d) a polypeptide consisting of the amino acid sequence of SEQ ID NO:2 from amino acid residue 224 (Glu) to amino acid residue 348 (Arg); (e) a polypeptide consisting of the amino acid sequence of SEQ ID NO:2 from amino acid residues 520 (Lys) to amino acid residue 543 (Arg); (f) a polypeptide consisting of the amino acid sequence of SEQ ID NO:2 from amino acid number 675 (Cys) to amino acid residue 709 (Cys); (g) a polypeptide consisting of the amino acid sequence of SEQ ID NO:2 from amino acid number 278 (Gln) to amino acid number 283 (Gln); (h) a polypeptide consisting of the amino acid sequence of SEQ ID NO:2 from amino acid number 311 (Ser) to amino acid number 316 (His); (i) a polypeptide consisting of the amino acid sequence of SEQ ID NO:2 from amino acid number 344 (Gln) to amino acid number 349 (Gln); (j) a polypeptide consisting of the amino acid sequence of SEQ ID NO:2 from amino acid number 521 (Glu) to amino acid number 526 (Glu); and (k) a polypeptide consisting of the amino acid sequence of SEQ ID NO:2 from amino acid number 523 (Gln) to amino acid number 528 (Glu), wherein the polypeptide elicits an immune response in the animal to produce the antibody; and isolating the antibody from the animal.

Within another aspect, the present invention provides an antibody produced by the method disclosed above, which binds to a zapop3 polypeptide. Within one embodiment, the antibody disclosed above is a monoclonal antibody. Within another aspect, the present invention provides an antibody which binds to a polypeptide as disclosed above.

Within another aspect, the present invention provides a method of detecting, in a test sample, the presence of an agonist of zapop3 protein activity, comprising: transfecting a zapop3-expressing cell, with a reporter gene construct that is responsive to a zapop3-stimulated cellular pathway; and adding a test sample; and comparing levels of response in the presence and absence of the test sample, by a biological or biochemical assay; and determining from the comparison, the presence of the agonist of zapop3 activity in the test sample.

These and other aspects of the invention will become evident upon reference to the following detailed description of the invention.

DETAILED DESCRIPTION OF THE INVENTION

Figure 1A:
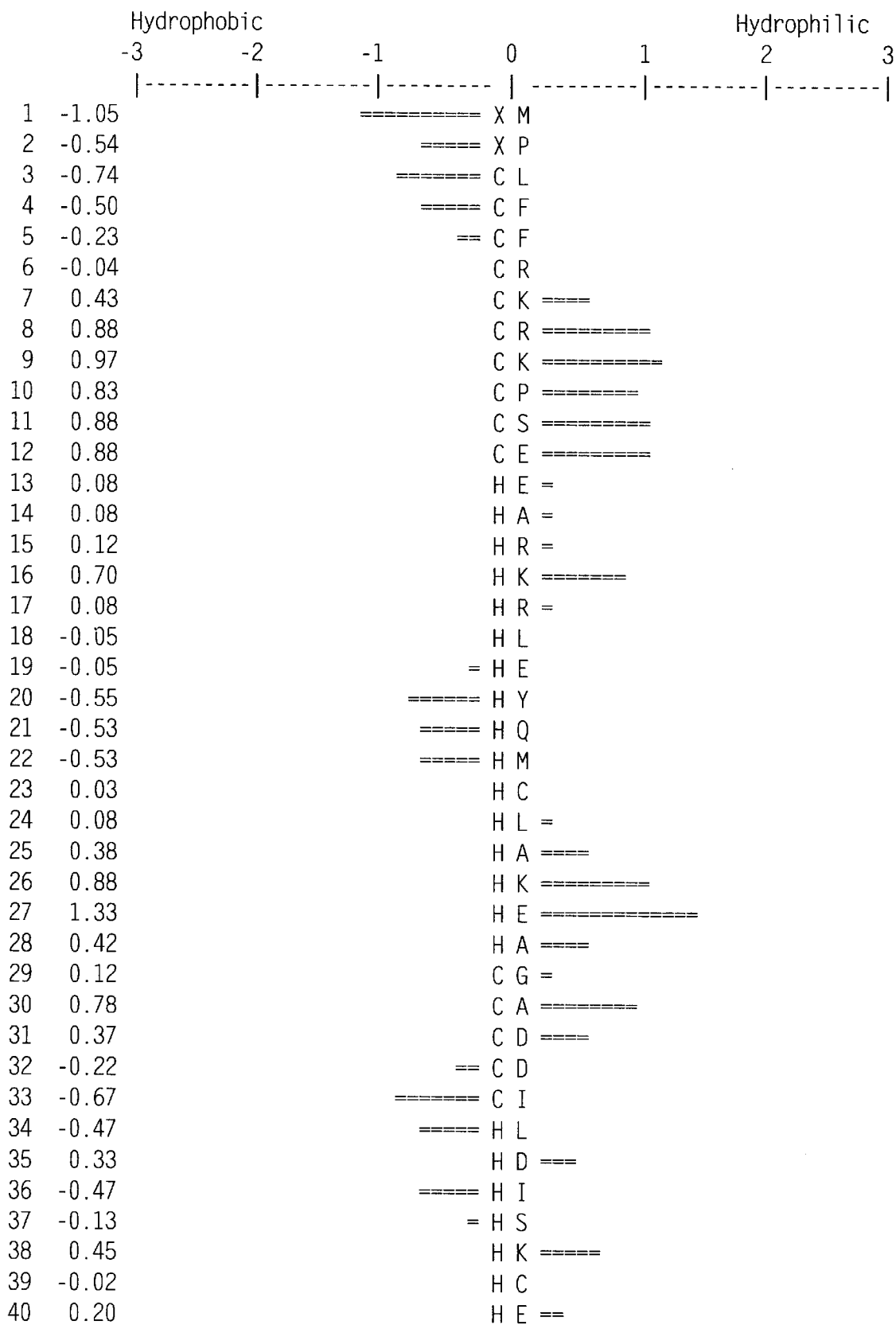
FIG. 1 is a hydrophobicity and secondary structure prediction plot of zapop3. The secondary structure prediction plot is based on Mehta, P. K. et al., *Protein Science* 4:2517–2525, 1995. The hydrophobicity plot is based on a sliding six-residue window, with buried G, S, and T residues and exposed H, Y, and W residues ignored; The hydrophobic ranking used was MIFLVWCGRSTAPYNKDEHQ (Trinquier, G., and Sanejuand, Y-H., *Protein Engineer.* 11:153–169, 1998).
Figure 1Q:
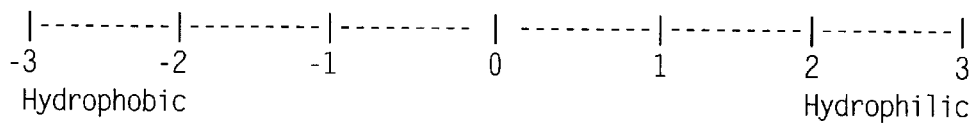

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGAGCTT-3' are 5'-AGCTTgagt-3' and 3'-tcgacTACC-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF. receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene.

Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide having partial homology to BRCA1 RING finger domain (Jensen, D. E. et al., *Oncogene* 16:1097–1112, 1998) and containing LRRs. Analysis of the tissue distribution of the mRNA corresponding to this novel DNA showed strong expression levels in heart and skeletal muscle, and low expression in other tissues. The polypeptide has been designated zapop3.

The novel zapop3 polypeptides of the present invention were initially identified by querying an EST database for proteins homologous to proteins having a RING finger sequence. The consensus RING finger motif is characterized by a cysteine motif of the formula:

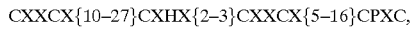

CXXCX{10–27}CXHX{2–3}CXXCX{5–16}CPXC, wherein X is any amino acid, C is Cysteine, H is Histidine, and {#–#} is the range of repetition of the preceding residue X. This cysteine motif occurs in all currently known RING finger proteins, such as, apoptosis inhibitor proteins (IAPs), and the like, and is unique to this family of proteins. These search criteria were compared to an EST database to identify novel proteins having homology to known RING finger proteins. The full sequence of the zapop3 polypeptide was obtained from a single clone believed to contain it, wherein the clone was obtained from a peripheral blood granulocyte library. Other libraries that might also be searched for such sequences include heart, skeletal muscle, pancreas, brain, stomach, colon, thyroid, and the like.

The nucleotide sequence of full-length zapop3 is described in SEQ ID NO:1, and its deduced amino acid sequence is described in SEQ ID NO:2. Sequence analysis revealed that zapop3 is a member of a diverse family of proteins that contain leucine rich repeats (LRRs), and is a member of a diverse family of proteins that are characterized by a RING finger domain. Zapop3, unlike known LRR or RING finger proteins, contains both the RING finger domain and LRRs in the same protein.

Analysis of the DNA encoding zapop3 polypeptide (SEQ ID NO:1) revealed an open reading frame encoding 723 amino acids (SEQ ID NO:2). Multiple alignment of zapop3 with BRCA1, and other members of the RING finger protein family, such as murine and human IAPs in addition to structural determinations based on amino acid sequences revealed the following regions, domains, and conserved motifs:

(1) N-terminal LRR region, corresponding to amino acid residues 1 (Met) to amino acid residue 223 (Leu) of SEQ ID NO:2. Within the LRR region there are 8 consecutive LRR motifs, ordered from N-terminus to C-terminus: "LRR-1" (corresponding to amino acids 30 (Ala) to 55 (Leu) of SEQ ID NO:2); "LRR-2" (corresponding to amino acids 56 (Gln) to 81 (Ala) of SEQ ID NO:2); "LRR-3" (corresponding to amino acids 82 (Thr) to 104 (Thr) of SEQ ID NO:2); "LRR-4" (corresponding to amino acids 105 (Ala) to 127 (Thr) of SEQ ID NO:2); "LRR-5" (corresponding to amino acids 128 (Gln) to 150 (Arg) of SEQ ID NO:2); "LRR-6" (corresponding to amino acids 151 (Ser) to 173 (Arg) of SEQ ID NO:2); "LRR-7" (corresponding to amino acids 174 (Thr) to 199 (Ala) of SEQ ID NO:2); and "LRR-8" (corresponding to amino acids 200 (Ile) to 223 (Leu) of SEQ ID NO:2).

(2) Central hydrophilic region, corresponding to amino acid residues 224 (Glu) to amino acid residue 348 (Arg) of SEQ ID NO:2.

(3) Alpha-helix rich region, corresponding to amino acid residues 349 (Gln) to amino acid residue 543 (Arg) of SEQ ID NO:2. Within this region is a short hydrophilic domain corresponding to amino acid residues 520 (Lys) to amino acid residue 543 (Arg) of SEQ ID NO:2.

(4) C-terminal region, corresponding to amino acid residues 544 (Gln) to amino acid residue 723 (Ser) of SEQ ID NO:2. Within this region is a RING finger domain corresponding to amino acid residues 675 (Cys) to amino acid residue 709 (Cys) of SEQ ID NO:2, which contains the RING finger consensus sequence described above.

The presence of conserved and low variance motifs generally correlates with or defines important structural regions in proteins. Regions of low variance (e.g., hydrophobic clusters) are generally present in regions of structural importance (Sheppard, P. et al., *Gene* 150:163–167, 1994). Such regions of low variance often contain rare or infrequent amino acids, such as Tryptophan. The regions flanking and between such conserved and low variance motifs may be more variable, but are often functionally significant because they may relate to or define important structures and activities such as binding domains, biological and enzymatic activity, signal transduction, tissue localization domains and the like. For example, the hydrophilic and C-terminal regions, described above may be functionally significant. Moreover, some domains, such as the RING finger domain and LRR motifs, have known biological activities, for example as protein binding or DNA binding domains (Wang, H. et al., *Oncogene* 15:143–157, 1997; Buchanan, S. and Gay, N., *Prog. Biophys. Molec. Biol.* 65:1–44, 1996; Brzovic, P. S. et al., *J. Biol. Chem.* 273:7795–7799, 1998). The corresponding polynucleotides encoding the zapop3 polypeptide regions, domains, motifs and residues and sequences described above are as shown in SEQ ID NO:1.

The conserved amino acids in the LRR region and the RING finger domain of zapop3 can be used as a tool to identify new family members. For instance, reverse transcription-polymerase chain reaction (RT-PCR) can be used to amplify sequences encoding the conserved RING finger motif from RNA obtained from a variety of tissue sources or cell lines. In particular, highly degenerate primers designed from the zapop3 polynucleotide sequences are useful for this purpose. Designing and using such degenerate primers may be readily performed by one skilled in the art. The present invention also provides polynucleotide molecules, including DNA and RNA molecules, that encode the zapop3 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zapop3 polypeptide of SEQ ID NO:2. Those skilled in the art will recognize that the degenerate sequence of SEQ ID NO:3 also provides all RNA sequences encoding SEQ ID NO:2 by substituting U for T. Thus, zapop3 polypeptide-encoding polynucleotides comprising nucleotide 1 to nucleotide 2169 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | | | | | | Degenerate Codon |
|---|---|---|---|---|---|---|---|---|
| Cys | C | TGC | TGT | | | | | TGY |
| Ser | S | AGC | AGT | TCA | TCC | TCG | TCT | WSN |
| Thr | T | ACA | ACC | ACG | ACT | | | ACN |
| Pro | P | CCA | CCC | CCG | CCT | | | CCN |
| Ala | A | GCA | GCC | GCG | GCT | | | GCN |
| Gly | G | GGA | GGC | GGG | GGT | | | GGN |
| Asn | N | AAC | AAT | | | | | AAY |
| Asp | D | GAC | GAT | | | | | GAY |
| Glu | E | GAA | GAG | | | | | GAR |
| Gln | Q | CAA | CAG | | | | | CAR |
| His | H | CAC | CAT | | | | | CAY |
| Arg | R | AGA | AGG | CGA | CGC | CGG | CGT | MGN |
| Lys | K | AAA | AAG | | | | | AAR |
| Met | M | ATG | | | | | | ATG |
| Ile | I | ATA | ATC | ATT | | | | ATH |
| Leu | L | CTA | CTC | CTG | CTT | TTA | TTG | YTN |
| Val | V | GTA | GTC | GTG | GTT | | | GTN |
| Phe | F | TTC | TTT | | | | | TTY |
| Tyr | Y | TAC | TAT | | | | | TAY |
| Trp | W | TGG | | | | | | TGG |
| Ter | . | TAA | TAG | TGA | | | | TRR |
| Asn\|Asp | B | | | | | | | RAY |
| Glu\|Gln | Z | | | | | | | SAR |
| Any | X | | | | | | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227, 1990). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences (e.g., >50 base pairs) is performed at temperatures of about 20–25° C. below the calculated $T_m$. For smaller probes (e.g., <50 base pairs) hybridization is typically carried out at the $T_m$ or 5–10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40–50% formamide, up to about 6×SSC, about 5× Denhardt's solution, zero up to about 10% dextran sulfate, and about 10–20 µg/ml denatured commercially-available carrier DNA. Generally, such stringent conditions include temperatures of 20–70° C. and a hybridization buffer containing up to 6×SSC and 0–50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of zapop3 RNA. Such tissues and cells are identified by Northern blotting (Thomas, *Proc. Natl. Acad. Sci. USA* 77:5201, 1980), and include heart and skeletal muscle. Total RNA can be prepared using guanidinium isothiocyanate extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding zapop3 polypeptides are then identified and isolated by, for example, hybridization or polymerase chain reaction (PCR) (Mullis, U.S. Pat. No. 4,683,202).

A full-length clone encoding zapop3 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zapop3, polypeptide fragments thereof, or other specific binding partners.

The polynucleotides of the present invention can also be synthesized using DNA synthesis machines, for example, by using the phosphoramidite method. A synthetic zapop3 gene can be constructed from a set of overlapping, complementary oligonucleotides, each of which is between 20 to 60 nucleotides long. Each internal section of the gene has complementary 3' and 5' terminal extensions designed to base pair precisely with an adjacent section. Thus, after the gene is assembled, process is completed by sealing the nicks along the backbones of the two strands with T4 DNA ligase. In addition to the protein coding sequence, synthetic genes can be designed with terminal sequences that facilitate insertion into a restriction endonuclease site of a cloning vector. Moreover, other sequences should can be added that contain signals for proper initiation and termination of transcription and translation. Alternatively, a specified set of partially overlapping oligonucleotides (40 to 100 nucleotides) can be used. After the 3' and 5' short overlapping complementary regions are paired, large gaps may still remain, but the base-paired regions are both long enough and stable enough to hold the structure together. The gaps are filled, and the DNA duplex is completed, via enzymatic DNA synthesis by *E coli* DNA polymerase I. After the enzymatic synthesis is completed, the nicks are sealed with T4 DNA ligase. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

Zapop3 polynucleotide sequences disclosed herein can also be used as probes or primers to clone 5' non-coding regions of a zapop3 gene. In view of the tissue-specific expression observed for zapop3 by Northern blotting, this gene region is expected to provide for heart- and skeletal muscle-specific expression. Promoter elements from a zapop3 gene could thus be used to direct the tissue-specific expression of heterologous genes in, for example, transgenic animals or patients treated with gene therapy. Cloning of 5' flanking sequences also facilitates production of zapop3 proteins by "gene activation" as disclosed in U.S. Pat. No. 5,641,670. Briefly, expression of an endogenous zapop3 gene in a cell is altered by introducing into the zapop3 locus a DNA construct comprising at least a targeting sequence, a regulatory sequence, an exon, and an unpaired splice donor site. The targeting sequence is a zapop3 5' non-coding sequence that permits homologous recombination of the construct with the endogenous zapop3 locus, whereby the sequences within the construct become operably linked with the endogenous zapop3 coding sequence. In this way, an endogenous zapop3 promoter can be replaced or supplemented with other regulatory sequences to provide enhanced, tissue-specific, or otherwise regulated expression.

The present invention further provides counterpart polypeptides and polynucleotides from other species (orthologs). These species include, but are not limited to mammalian, avian, amphibian, reptile, fish, insect and other vertebrate and invertebrate species. Of particular interest are zapop3 polypeptides from other mammalian species, including murine, porcine, ovine, bovine, canine, feline, equine, and other primate polypeptides. Orthologs of human zapop3 can be cloned using information and compositions provided by the present invention in combination with conventional cloning techniques. For example, a cDNA can be cloned using mRNA obtained from a tissue or cell type that expresses zapop3 as disclosed herein. Suitable sources of mRNA can be identified by probing Northern blots with probes designed from the sequences disclosed herein. A library is then prepared from mRNA of a positive tissue or cell line. A zapop3-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zapop3 sequence disclosed herein. Within an additional method, the cDNA library can be used to transform or transfect host cells, and expression of the cDNA of interest can be detected with an antibody to zapop3 polypeptide. Similar techniques can also be applied to the isolation of genomic clones.

Those skilled in the art will recognize that the sequence disclosed in SEQ ID NO:1 represents a single allele of human zapop3 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zapop3 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art. The corresponding polynucleotides encoding the zapop3 polypeptide regions, domains, motifs, residues and sequences described above are as shown in SEQ ID NO:1.

The present invention also provides isolated zapop3 polypeptides that are substantially similar to the polypeptides of SEQ ID NO:2 and their orthologs. The term "substantially similar" is used herein to denote polypeptides having 50%, preferably 60%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs.) Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zapop3. The FASTA algorithm is described by Pearson and Lipman, *Proc. Nat'l Acad. Sci. USA* 85:2444, 1988; and by Pearson, *Meth. Enzymol.* 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.*, supra.

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The BLOSUM62 table (Table 3) is an amino acid substitution matrix derived from about 2,000 local multiple

TABLE 3

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| A | 4  |    |    |    |    |    |    |    |    |    |    |    |    |    |    |    |    |    |    |   |
| R | -1 | 5  |    |    |    |    |    |    |    |    |    |    |    |    |    |    |    |    |    |   |
| N | -2 | 0  | 6  |    |    |    |    |    |    |    |    |    |    |    |    |    |    |    |    |   |
| D | -2 | -2 | 1  | 6  |    |    |    |    |    |    |    |    |    |    |    |    |    |    |    |   |
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 | alignments of protein sequence segments, representing highly conserved regions of more than 500 groups of related proteins (Henikoff and Henikoff, *Proc. Nat'l Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zapop3 polypeptides or substantially homologous zapop3 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a linker peptide of up to about 20–25 residues, or an affinity tag. The present invention thus includes polypeptides of from about 698 to about 750 amino acid residues that comprise a sequence that is at least 80%, preferably at least 90%, and more preferably 95% or more identical to the corresponding region of SEQ ID NO:2. Polypeptides comprising affinity tags can further comprise a proteolytic cleavage site between the zapop3 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a zapop3 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zapop3 polypeptide fusions can be expressed in genetically engineered cells to produce a variety of multimeric zapop3 analogs. Auxiliary domains can be fused to zapop3 polypeptides to target them to specific cells, tissues, or macromolecules (e.g., collagen). For example, a zapop3 polypeptide or protein could be targeted to a predetermined cell type by fusing a zapop3 polypeptide to a ligand that specifically binds to a receptor on the surface of the target cell. In this way, polypeptides and proteins can be targeted for therapeutic or diagnostic purposes. A zapop3 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zapop3 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor or other biological or functional interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related LRR-containing and RING finger proteins.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zapop3 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., that induce proliferation, transformation or apoptosis) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 or that retain the signal transduction or protein-protein or DNA binding properties of the wild-type zapop3 protein. For example, one can make a zapop3 "protein binding fragment" by preparing a variety of polypeptides that are substantially homologous to the LRR region or RING finger domain and retain protein-binding activity of the wild-type zapop3 protein. Such polypeptides may include additional amino acids from, for example, part or all of the N-terminal and C-terminal domains. Such polypeptides may also include additional polypeptide segments as generally disclosed herein such as labels, affinity tags, and the like.

For any zapop3 polypeptide, including variants and fusion proteins, one of ordinary skill in the art can readily generate a fully degenerate polynucleotide sequence encoding that variant using the information set forth in Tables 1 and 2 above.

The zapop3 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., N.Y., 1987.

In general, a DNA sequence encoding a zapop3 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zapop3 polypeptide into the secretory pathway of a host cell, a secretory signal sequence (also known as a leader sequence, prepro sequence or pre sequence) is provided in the expression vector. The secretory signal sequence may be that of zapop3, or may be derived from another secreted protein (e.g., t-PA) or synthesized de novo. The secretory signal sequence is operably linked to the zapop3 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

To direct the export of a zapop3 polypeptide from the host cell, the zapop3 DNA is linked to a second DNA segment encoding a secretory peptide, such as a t-PA secretory peptide. To facilitate purification of the secreted receptor polypeptide, a C-terminal extension, such as a poly-histidine tag, substance P, Flag peptide (Hopp et al., *Bio/Technology* 6:1204–1210, 1988; available from Eastman Kodak Co., New Haven, Conn.) or another polypeptide or protein for which an antibody or other specific binding agent is available, can be fused to the zapop3 polypeptide.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., Focus 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784, 950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601, 978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. The second method of making recombinant zapop3 baculovirus utilizes a transposon-based system described by Luckow (Luckow et al., *J. Virol.* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zapop3 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zapop3. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6 1990; Bonning, B. C. et al., *J. Gen. Virol.* 75:1551–6, 1994; and, Chazenbalk, G. D., and Rapoport, B., *J. Biol. Chem.* 270:1543–9, 1995. In such transfer vector constructs, a short or long version of the basic protein promoter can be used. Moreover, transfer vectors can be constructed which replace the native zapop3 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zapop3 secretory signal sequence. In addition, transfer vectors can include an in-frame fusion with DNA encoding an epitope tag at the C- or N-terminus of the expressed zapop3 polypeptide, for example, a Glu-Glu epitope tag (Grussenmeyer, T. et al., *Proc. Natl. Acad. Sci.* 82:7952–4, 1985). Using a technique known in the art, a transfer vector containing zapop3 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zapop3 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen, San Diego, Calif.) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the zapop3 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zapop3 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zapop3 polypeptides (or chimeric zapop3 polypeptides) can be purified using fractionation and/or conventional purification methods and media. For example, the particular purification methods for TIGR, described in Nguyen, supra., are exemplary, and can be adapted to zapop3 polypeptide by one of ordinary skill in the art using methods described below. An exemplary purification method for protein constructs having an affinity tag such as an N-terminal or C-terminal FLAG tag produced from mammalian cells, such as BHK cells, involves using an antibody to the FLAG tag epitope to purify the zapop3 protein. Conditioned media from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then concentrated using an Amicon (Beverly, Mass.) DC 10L concentrator fitted with an A/G Tech (Needham, Mass.) hollow fiber cartridge with a 15 sq. ft. 3000 kDa cutoff membrane. The concentrated material is again sterile-filtered with the Gelman filter as described above. A aliquot of anti-Flag Sepharose (Eastman Kodak, Rochester, N.Y.) is added to the sample for batch adsorption and the mixture is gently agitated on a Wheaton (Millville, N.J.) roller culture apparatus for 18.0 h at 4° C.

The mixture is then poured into a 5.0×20.0 cm Econo-Column (Bio-Rad, Laboratories, Hercules, Calif.) and the gel is washed with 30 column volumes of phosphate buffered saline (PBS). The unretained flow-through fraction is discarded. Once the absorbance of the effluent at 280 nM is less than 0.05, flow through the column is reduced to zero and the anti-Flag Sepharose gel is washed with 2.0 column volumes of PBS containing 0.2 mg/ml of Flag peptide, (SEQ ID NO:4) (Eastman Kodak). After 1.0 hour at 4° C., flow is resumed and the eluted protein is collected. This fraction is referred to as the peptide elution. The anti-Flag Sepharose gel is washed with 2.0 column volumes of 0.1 M glycine, pH 2.5, and the glycine wash is collected separately. The pH of the glycine-eluted fraction is adjusted to 7.0 by the addition of a small volume of 10×PBS and stored at 4° C.

The peptide elution is concentrated to 5.0 ml using a 5,000 molecular weight cutoff membrane concentrator (Millipore, Bedford, Mass.) according to the manufacturer's instructions. The concentrated peptide elution is then separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC system (PerSeptive BioSystems, Framingham, Mass.). Two-ml fractions are collected and the absorbance at 280 nM is monitored. The first peak of material absorbing at 280 nM and eluting near the void volume of the column is collected.

SDS-PAGE, Western analysis, amino acid analysis and N-terminal sequencing can be done to the purified protein. Protein concentration can be determined by BCA analysis (Pierce, Rockford, Ill.).

Protein purification methods also include, fractionation of samples by ammonium sulfate precipitation and acid or chaotrope extraction. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their biochemical, structural, and biological properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid zapop3 proteins, are constructed using regions or domains of the inventive zapop3 in combination with those of other RING or LRR family proteins (e.g. BRCA1, murine or human IAP), or heterologous proteins (Sambrook et al., ibid., Altschul et al., ibid., Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between zapop3 of the present invention with the functionally equivalent domain(s) from another family member, such as BRCA1. Such domains include, but are not limited to, the LRR region, individual LRRs (LRR 1–8), hydrophilic region, alpha-helical region, short, hydrophilic domain, C-terminal region, and the RING finger domain described herein. Such fusion proteins would be expected to have a biological functional profile that is the same or similar to polypeptides of the present invention or other known RING protein family members, depending on the fusion constructed. Moreover, such fusion proteins may exhibit other properties as disclosed herein.

Standard molecular biological and cloning techniques can be used to swap the equivalent domains between the zapop3 polypeptide and those polypeptides to which they are fused. Generally, a DNA segment that encodes a domain of interest, e.g., a zapop3 domain described herein, is operably linked in frame to at least one other DNA segment encoding an additional polypeptide (for instance a domain or region from another RING finger protein, such as BRCA1), and inserted into an appropriate expression vector, as described herein.

Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising an N-terminal region containing LRRs, operably connected to a central hydrophilic region, operably connected to an alpha-helical region, operably connected to a, C-terminal region containing a RING finger domain. Such fusion proteins can be expressed, isolated, and assayed for activity as described herein.

Zapop3 polypeptides or fragments thereof may also be prepared through chemical synthesis. zapop3 polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem.* 34:595, 1970. After the entire synthesis of the desired peptide on a solid support, the peptide-resin is with a reagent which cleaves the polypeptide from the resin and removes most of the side-chain protecting groups. Such methods are well established in the art.

The activity of molecules of the present invention can be measured using a variety of assays that measure proliferation, morphogensis, apoptosis, or transformation. Such assays are well known in the art.

The polypeptides, nucleic acids and/or antibodies of the present invention can be used in treatment of disorders associated with myocardial infarction, congestive heart failure, hypertrophic cardiomyopathy and dilated cardiomyopathy. Molecules of the present invention may also be useful for limiting infarct size following a heart attack, aiding in recovery after heart transplantation, promoting angiogenesis and wound healing following angioplasty or endarterectomy, to develop coronary collateral circulation, for revascularization in the eye, for complications related to poor circulation such as diabetic foot ulcers, for stroke, following coronary reperfusion using pharmacologic methods, and other indications where angiogenesis is of benefit. Molecules of the present invention may be useful for improving cardiac function, either by inducing cardiac myocyte neogenesis and/or hyperplasia, by inducing coronary collateral development, or by inducing remodeling of necrotic myocardial area. Other therapeutic uses for the present invention include induction of skeletal muscle neogenesis and/or hyperplasia, kidney regeneration and/or for treatment of systemic and pulmonary hypertension.

Zapop3 can be assayed for apoptosis inhibitory activity using the methods of Ambrosini, G. et al., *Nature Med.* 3:917–921, 1997. Briefly, cDNAs encoding Bcl-2 and zapop3 are cloned into mammalian expression vector pcDNA3 (Invitrogen) and transfected into the IL-3-dependant murine pre-B-cell line, BaF3, using standard molecular biology techniques (Ausubel et al., supra.; Palacios and Steinmetz, *Cell* 41:727–734, 1985; Mathey-Prevot et al., *Mol. Cell. Biol.* 6: 4133–4135, 1986; Ascaso, R. et al., *Eur. J. Immunol.* 24:537–541, 1994). Stable cell lines are selected and cloned by methods disclosed herein, for example by G418 selection. To assess the effect of zapop3 on apoptosis, survival of cells co-expressing Bcl-2 and zapop3 is measured under conditions where apoptosis is normally induced, i.e., when IL-3 is withdrawn from the cell culture medium. Viability can be measured, for, example, by trypan blue staining. Wild-type Baf3 cells, and cells expressing only Bcl-2 are used as positive controls for apoptosis. In the presence of zapop3, inhibition of apoptosis is shown as increased survival of cells expressing zapop3 relative to the control cells.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: (i) adenovirus can accommodate relatively large DNA inserts; (ii) can be grown to high-titer; (iii) infect a broad range of mammalian cell types; and (iv) can be used with a large number of different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete). the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are El deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are a particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

The activation of zapop3 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzamol.* 228:84–108, 1997; Arimilli, S. et al., *J. Immunol. Meth.* 212:49–59, 1998; Van Liefde, I. Et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including agonists, ligands, or antagonists of the zapop3 polypeptide. Preferably, the microphysiometer is used to measure responses of a zapop3-expressing eukaryotic cell, compared to a control eukaryotic cell that does not express zapop3 polypeptide. Zapop3-expressing eukaryotic cells comprise cells into which zapop3 has been transfected, as described herein, creating a cell that is responsive to zapop3-modulating stimuli; or cells naturally expressing zapop3, such as zapop3-expressing cells derived from spleen, testis, muscle or heart tissue. Differences, measured by a change in extracellular acidification, for example, an increase or diminution in the response of cells expressing zapop3, relative to a control, are a direct measurement of zapop3 modulated cellular responses. Moreover, such zapop3-modulated responses can be assayed under a variety of stimuli. Also, using the microphysiometer, there is provided a method of identifying agonists and antagonists of zapop3 polypeptide, comprising providing cells expressing a zapop3 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Antagonists and agonists, including the natural ligand for zapop3 polypeptide, can be rapidly identified using this method.

In view of the tissue distribution observed for zapop3, agonists (including the natural substrate/cofactor/etc.) and antagonists have enormous potential in both in vitro and in vivo applications. Compounds identified as zapop3 agonists are useful for stimulating growth of heart, skeletal muscle, immune and hematopoietic cells in vitro and in vivo. For example, zapop3 and agonist compounds are useful as components of defined cell culture media, and may be used alone or in combination with other cytokines and hormones to replace serum that is commonly used in cell culture. Agonists are thus useful in specifically promoting the growth and/or development of cardiac cells, skeletal muscle cells and other cells in culture. Moreover, zapop3 agonist, or antagonist, may be used in vitro in an assay to measure stimulation of colony formation from isolated primary bone marrow cultures. Such assays are well known in the art.

Antagonists are also useful as research reagents for characterizing sites of protein-protein interaction. Inhibitors of zapop3 activity (zapop3 antagonists) include anti-zapop3 antibodies as well as other peptidic and non-peptidic agents (including ribozymes).

Zapop3 can also be used to identify modulators (e.g, agonists or antagonists) of its activity. Test compounds are added to the assays disclosed herein to identify compounds that inhibit or stimulate the activity of zapop3. In addition to those assays disclosed herein, samples can be tested for inhibition/stimulation of zapop3 activity within a variety of assays designed to measure zapop3 binding, dimerization, heterodimerization, DNA binding or the stimulation/ inhibition of zapop3-dependent cellular responses. For example, zapop3-expressing cell lines can be transfected with a reporter gene construct that is responsive to a zapop3-stimulated cellular pathway. Reporter gene constructs of this type are known in the art, and will generally comprise a zapop3-DNA response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts or conditioned media from various cell types are tested for the ability to enhance the activity of zapop3 signal transduction as evidenced by a increase in zapop3 stimulation of reporter gene expression. Assays of this type will detect compounds that directly stimulate zapop3 signal transduction activity through binding the upstream receptor or by otherwise stimulating part of the signal cascade in which zapop3 is involved. As such, there is provided a method of identifying agonists of zapop3 polypeptide, comprising providing cells expressing zapop3 responsive to a zapop3 pathway, culturing a first portion of the cells in the absence of a test compound, culturing a second portion of the cells in the presence of a test compound, and detecting a increase in a cellular response of the second portion of the cells as compared to the first portion of the cells. Moreover a third cell, containing the reporter gene construct described above, but not expressing zapop3 polypeptide, can be used as a control cell to assess non-specific, or non-zapop3-mediated, stimulation of the reporter. Agonists are useful to stimulate or increase zapop3 polypeptide function.

Moreover, compounds or other samples can be tested for direct blocking of zapop3 binding to another protein, e.g., a heterodimer described below, using zapop3 tagged with a detectable label (e.g., $^{125}$I, biotin, horseradish peroxidase, FITC, and the like). Within assays of this type, the ability of a test sample to inhibit the binding of labeled zapop3 to the other protein is indicative of inhibitory activity, which can be confirmed through secondary assays. Proteins used within binding assays may be cellular proteins or isolated, immobilized proteins.

A zapop3 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to (any specific uses?, affinity purify ligand, in vitro assay tool, antagonist). For use in assays, the chimeras are bound to a support via the $F_c$ region and used in an ELISA format.

A zapop3 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

Zapop3 polypeptides can also be used to prepare antibodies that bind to zapop3 epitopes, peptides or polypeptides. The zapop3 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zapop3 polypeptide (e.g., SEQ ID NO:2). Polypeptides comprising a larger portion of a zapop3 polypeptide, i.e., from 30 to 10 residues up to the entire length of the amino acid sequence are included. Antigens or immunogenic epitopes can also include attached tags, adjuvants and carriers, as described herein. Suitable antigens include the zapop3 polypeptide encoded by SEQ ID NO:2 from amino acid number 1 (Met) to amino acid number 723 (Ser), or a contiguous 9 to 723 amino acid amino acid fragment thereof. Preferred peptides to use as antigens are the N-terminal LRR region, central hydrophilic region, alpha helical rich region, short hydrophilic domain, C-terminal region and the RING finger domain, disclosed herein, and zapop3 hydrophilic peptides such as those predicted by one of skill in the art from a hydrophobicity plot, determined for example, from a hydrophobicity profile such as that shown in the Figure. Zapop3 hydrophilic peptides include peptides comprising amino acid sequences selected from the group consisting of: (1) amino acid number 278 (Gln) to amino acid number 283 (Gin) of SEQ ID NO:2; (2) amino acid number 311 (Ser) to amino acid number 316 (His) of SEQ ID NO:2; (3) amino acid number 344 (Gln) to amino acid number 349 (Gln) of SEQ ID NO:2; (4) amino acid number 521 (Glu) to amino acid number 526 (Glu) of SEQ ID NO:2; and (5) amino acid number 523 (Gln) to amino acid number 528 (Glu) of SEQ ID NO:2. In addition, conserved motifs, and variable regions between conserved motifs of zapop3 are suitable antigens. Antibodies generated from this immune response. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zapop3 polypeptide or a fragment thereof. The immunogenicity of a zapop3 polypeptide may be increased through the use of an adjuvant, such as alum (aluminum hydroxide) or Freund's complete or incomplete adjuvant. Polypeptides useful for immunization also include fusion polypeptides, such as fusions of zapop3 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-zapop3 antibodies herein specifically bind if they bind to a zapop3 polypeptide, peptide or epitope with an affinity at least 10-fold greater than the binding affinity to control (non-zapop3) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Whether anti-zapop3 antibodies do not significantly cross-react with related polypeptide molecules is shown, for example, by the antibody detecting zapop3 polypeptide but not known related polypeptides using a standard Western blot analysis (Ausubel et al., ibid.). Examples of known related polypeptides are those disclosed in the prior art, such as known orthologs, and paralogs, and similar known members of a protein family, Screening can also be done using non-human zapop3, and zapop3 mutant polypeptides. Moreover, antibodies can be "screened against" known related polypeptides, to isolate a population that specifically binds to the inventive zapop3 polypeptides. For example, antibodies raised to zapop3 are adsorbed to related polypeptides adhered to insoluble matrix; antibodies specific to zapop3 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984. Specifically binding anti-zapop3 antibodies can be detected by a number of methods in the art, and disclosed below.

A variety of assays known to those skilled in the art can be utilized to detect antibodies which specifically bind to zapop3 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zapop3 protein or polypeptide.

Alternative techniques for generating or selecting antibodies useful herein include in vitro exposure of lymphocytes to zapop3 protein or peptide, and selection of antibody display libraries in phage or similar vectors (for instance, through use of immobilized or labeled zapop3 protein or peptide). Genes encoding polypeptides having potential zapop3 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zapop3 sequences disclosed herein to identify proteins which bind to zapop3. These "binding polypeptides" which interact with zapop3 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of zapop3 polypeptides; for detecting or quantitating soluble zapop3 polypeptides as marker of underlying pathology or disease. These binding polypeptides can also act as zapop3 "antagonists" to block zapop3 binding and signal transduction in vitro and in vivo. These anti-zapop3 binding polypeptides would be useful for inhibiting zapop3 activity or protein-binding.

Antibodies to zapop3 may be used for tagging cells that express zapop3; for isolating zapop3 by affinity purification; for diagnostic assays for determining circulating levels of zapop3 polypeptides; for detecting or quantitating soluble zapop3 as marker of underlying pathology or disease; in analytical methods employing FACS; for screening expression libraries; for generating anti-idiotypic antibodies; and as neutralizing antibodies or as antagonists to block zapop3 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zapop3 or fragments thereof may be used in vitro to detect denatured zapop3 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zapop3 polypeptides or anti-zapop3 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zapop3-cytokine fusion proteins or antibody-cytokine fusion proteins can be used for enhancing in vivo killing of target tissues (for example, blood and bone marrow cancers), if the zapop3 polypeptide or anti-zapop3 antibody targets the hyperproliferative blood or bone marrow cell (See, generally, Hornick et al., *Blood* 89:4437–47, 1997). They described fusion proteins enable targeting of a cytokine to a desired site of action, thereby providing an elevated local concentration of cytokine. Suitable zapop3 polypeptides or anti-zapop3 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

Moreover, such conjugates can be used as diagnostics for human disease. For example, labeled conjugates and anti-zapop3 antibodies can be used to identify diseased tissues, cells, cancers, necrosis, and the like, that over-express or under-express zapop3 relative to a normal non-diseased control. Histological methods known in the art, and other assays described herein can be used with these conjugates to identify diseased tissues.

In yet another embodiment, if the zapop3 polypeptide or anti-zapop3 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Molecules of the present invention can be used to identify and isolate proteins that bind or heterodimerize with zapop3. For example, proteins and polypeptides of the present invention can be immobilized on a column and cell lysatepreparations run over the column (*Immobilized Affinity Lipand Techniques*, Hermanson et al., eds., Academic Press, San Diego, Calif., 1992, pp.195–202). Proteins and polypeptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cellular proteins can be identified. For example, a zapop3 protein-binding polypeptide, such as the LRR region or RING finger domain disclosed herein, can also be used for purification of a heterodimeric protein to which zapop3 binds. The zapop3 protein-binding polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids or cell lysates containing the heterodimeric protein are passed through the column one or more times to allow the heterodimeric protein to bind to the zapop3 protein-binding polypeptide. The heterodimeric protein is then eluted using changes in salt concentration, chaotropic agents (guanidine HCl), or pH to disrupt protein-protein binding.

The molecules of the present invention will be useful to identify cancers that over-express zapop3 or express mutant forms of the polypeptide. The prolypeptides, nucleic acid and/or antibodies of the present invention can be used in treatment of disorders associated with cancer. The molecules of the present invention can be used to identify, modulate, treat and/or prevent development of pathological conditions in such diverse tissue as heart and skeletal muscle. In particular, certain cancers may be amenable to such diagnosis, treatment or prevention.

For example, mutations in the RING finger domain in the breast cancer susceptibility gene, BRCAI, correspond with inability of the protein to dimerize, and are linked to certain breast cancers (Brzovic, P. S. et al., supra. 273). Similarly, as another member of the RING finger family, zapop3 mutations or elevated expression may be associated with specific cancers. Thus, zapop3 polynucleotides and antibodies, described herein, can be used to identify such cancers, serving as a diagnostic for cancer susceptibility, as well as treat through gene therapy.

Using methods known in the art, antibodies to zapop3 and zapop3 polynucleotides can be radiolabeled, fluorescent or chemically labeled and used in histological assays to detect elevated zapop3 present in biopsies. Zapop3 antibodies and zapop3 polynucleotides of the present invention are useful for measuring changes in levels of expression of zapop3 polypeptides. Because zapop3 expression is restricted to specific tissues (i.e., heart and skeletal muscle, with low expression in other tissues), changes in expression levels could be used to monitor metabolism within these tissues. For example, increases in expression and/or transcription of zapop3 polypeptides and polynucleotides, may be predictive for increased cell proliferation of tumor cells. Furthermore, expression of zapop3 in tissue not normally expressing zapop3, for example, ovary and lung, may be indicative of metastasis of tumor cells.

Zapop3 may be demonstrated to be expressed differentially in certain epithelial tissues and carcinomas, particularly in lung, stomach, colon, esophagus, or intestine. Differential expression is the transient expression, or lack thereof, of specific genes, proteins or other phenotypic properties (known as differentiation markers) that occur during the progress of maturation in a cell or tissue. A set of differentiation markers is defined as one or more phenotypic properties that can be identified and are specific to a particular cell type. Thus, pluripotent stem cells that can regenerate without commitment to a lineage express a set of differentiation markers that are lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. Thus, Zapop3 expression can be used as a differentiation marker in normal and tumor tissues to determine the stage of the tumor or maturity of a cell.

A set of differentiation markers is defined as one or more phenotypic properties that can be identified and are specific to a particular cell type. Differentiation markers are transiently exhibited at various stages of cell lineage. Pluripotent stem cells that can regenerate without commitment to a lineage express a set of differentiation markers that are lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. The activity of molecules of the present invention can be measured using a variety of assays that measure proliferation and/or differentiation of specific cell types, regulation of second messenger levels and chemokine and neurotransmitter release. Such assays are well known in the art and described herein.

Additional methods using probes or primers derived, for example, from the nucleotide sequences disclosed herein can also be used to detect zapop3 expression in a patient sample, such as a tumor biopsy, stomach, lung, blood, saliva, tissue sample, or the like. For example, probes can be hybridized to tumor tissues and the hybridized complex detected by in situ hybridization. Zapop3 sequences can also be detected by PCR amplification using cDNA generated by reverse translation of sample mRNA as a template (*PCR Primer A Laboratory Manual*, Dieffenbach and Dveksler, eds., Cold Spring Harbor Press, 1995). When compared with a normal control, both increases or decreases of zapop3 expression in a patient sample, relative to that of a control, can be monitored and used as an indicator or diagnostic for disease.

Polynucleotides encoding zapop3 polypeptides are useful within gene therapy applications where it is desired to increase or inhibit zapop3 activity. If a mammal has a mutated or absent zapop3 gene, the zapop3 gene can be introduced into the cells of the mammal. In one embodiment, a gene encoding a zapop3 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Sarnulski et al., *J. Virol.* 61:3096–101, 1987; Samulski et al., *J. Virol.* 63:3822–8, 1989).

In another embodiment, a zapop3 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Pat. Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zapop3 gene transcription, such as to inhibit cell proliferation in vivo. Polynucleotides that are complementary to a segment of a zapop3-encoding polynucleotide (e.g., a polynucleotide as set forth in SEQ ID NO:1) are designed to bind to zapop3-encoding mRNA and to inhibit translation of such mRNA. Such antisense polynucleotides are used to inhibit expression of zapop3 polypeptide-encoding genes in cell culture or in a subject.

The present invention also provides reagents which will find use in diagnostic applications. For example, the zapop3 gene, a probe comprising zapop3 DNA or RNA or a subsequence thereof can be used to determine if the zapop3 gene is present on chromosome 9 or if a mutation has occurred. Zapop3 is located at the 9q34.11 region of chromosome 9 (See, Example 3). Detectable chromosomal aberrations at the zapop3 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, fluorescence in situ hybridization methods, short tandem repeat (STR) analysis employing PCR techniques, and other genetic linkage analysis techniques known in the art (Sambrook et al., ibid.; Ausubel et. al., ibid. Marian, Chest 108:255–65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The zapop3 gene is located at the 9q34.11 region of chromosome 9. Several genes of known function map to this region. For example, the CAIN oncogene (CAN), whose aberrant transcription is linked to acute myeloid leukemia, and is also essential for proper embryonic development, maps to 9q34.1 ((Pilz, A. et al., Genomics 25:139–149, 1995; Van Deursen, J. et al., EMBO J. 15:5774–5583, 1996; Von Lindern, M. et al., Molec. Cell Biol. 10:4016–4026, 1990). The zapop3 polynucleotide probes of the present invention can be used to detect abnormalities or genotypes associated with CAN such as those that are implicated in acute myeloid leukemia, or to identify heterozygous carriers of a defective CAN gene for genetic testing. In addition, zapop3 polynucleotide probes can be used to detect abnormalities or genotypes associated with retinitis pigmentosa-deafness syndrome 1, an autosomal dominant mutation on chromosome 9 at 9q34 (Kenna, P. et al., Brit. J. Ophthal. 81:207–213, 1997). Further, zapop3 polynucleotide probes can be used to detect abnormalities or genotypes associated with chronic myelogenous and myelocytic leukemias, where the ABL oncogene is located (9q34. 1). For example, a cromosome 9 translocation at this locus, (with BRCA1 on chromosome 22) is present in over 90% of chronic myelogenous leukemias, and 25030% of adult lymphoblastic leukemias and (with Philadelphia chromosome) in chronic myelocytic leukemias (Bernards, A. et al., Molec. Cell. Biol. 7:3231–3236, 1987; Haas, O. A. et al., Nature 359:414–416, 1992; de Klein, A. et al., Nature 300:765–767, 1982). Moreover, amongst other genetic loci, those for Tuberous Sclerosis (9q34), C5 complement deficiency (9q34.1), all manifest themselves in human disease states as well as map to this region of the human genome. See the Online Mendellian Inheritance of Man (OMIM) gene map, and references therein, for this region of chromosome 9 on a publicly available WWW server (http://www3.ncbi.nlm.nih.gov/htbin-post/Omim/getmap?chromosome=9q34.11). All of these serve as possible candidate genes for an inheritable disease which show linkage to the same chromosomal region as the zapop3 gene.

Similarly, defects in the zapop3 locus itself may result in a heritable human disease state. For example, in retinitis pigmentosa-deafness syndrome 1, described above, (Kenna, P. et al., supra.), patients have abnormal skeletal muscle histology, electromyography, and electrocardiography. As zapop3 is highly expressed in both heart and skeletal muscle, defects in zapop3 polypeptide may directly or indirectly cause symptoms of this disease, for example, by improperly binding with a heterodimeric protein important for normal cell function. Molecules of the present invention, such as the polypeptides, antagonists, agonists, polynucleotides and antibodies of the present invention would aid in the detection, diagnosis prevention, and treatment associated with a zapop3 genetic defect.

Mice engineered to express the zapop3 gene, referred to as "transgenic mice," and mice that exhibit a complete absence of zapop3 gene function, referred to as "knockout mice," may also be generated (Snouwaert et al., Science 257:1083, 1992; Lowell et al., Nature 366:740–42, 1993; Capecchi, M. R., Science 244: 1288–1292, 1989; Palmiter, R. D. et al. Annu Rev Genet. 20: 465–499, 1986). For example, transgenic mice that over-express zapop3, either ubiquitously or under a tissue-specific or tissue-restricted promoter can be used to ask whether over-expression causes a phenotype. For example, over-expression of a wild-type zapop3 polypeptide, polypeptide fragment or a mutant thereof may alter normal cellular processes, resulting in a phenotype that identifies a tissue in which zapop3 expression is functionally relevant and may indicate a therapeutic target for the zapop3, its agonists or antagonists. For example, preferred transgenic mice to engineer are ones that over-expresses the entire zapop3 polypeptide, or polypeptides comprising the the N-terminal region containing the LRRs, or the RING-finger domain. Moreover, such over-expression may result in a phenotype that shows similarity with human diseases. Similarly, knockout zapop3 mice can be used to determine where zapop3 is absolutely required in vivo. The phenotype of knockout mice is predictive of the in vivo effects of that a zapop3 antagonist, such as those described herein, may have. The human zapop3 cDNA can be used to isolate murine zapop3 mRNA, cDNA and genomic DNA, which are subsequently used to generate knockout mice. These mice may be employed to study the zapop3 gene and the protein encoded thereby in an in vivo system, and can be used as in vivo models for corresponding human diseases. Moreover, transgenic mice expression of zapop3 antisense polynucleotides or ribozymes directed against zapop3, described herein, can be used analogously to transgenic mice described above.

The invention is further illustrated by the following non-limiting examples.

EXAMPLES

Example 1

Identification of Zagop3

A. Using an EST Sequence to Obtain Full-length Zapop3

Scanning of translated granulocyte and PBL DNA databases using RING finger domain as a query resulted in identification of an expressed sequence tag (EST) sequence. The initial EST sequence was contained in a plasmid, and contained a partial 3' sequence. 5'RACE was carried out with primers ZC9,739 (AP1) (SEQ ID NO:5) and ZC16,257 (SEQ ID NO:6) using skeletal muscle cDNA prepared from skeletal muscle RNA (Clontech) using a Marathon cDNA kit (Clontech). PCR conditions were as follows: one cycle at 94° C. for 2'; 5 cycles at 94° C. for 20", and 72° C. for 2'; 30 cycles at 94° C. for 20", 66° C. for 20", 72° C. for 2'; one cycle at 72° C. for 5'; followed by 4° C. hold.

Using 5 µl of a 1:100 dilution of the initial RACE reaction, nested RACE was carried out with primers ZC9,719 (AP2) (SEQ ID NO:7) and ZC16,568 (SEQ ID NO:8). PCR conditions were as follows: one cycle at 94° C. for 2'; 18 cycles at 94° C. for 30", 56° C. for 20", 72° C. for 2'; one cycle at 72° C. for 5'; followed by 4° C. hold. The nested PCR reaction was electrophoresed on a 1.5% agarose gel and a 1 kb band was excised and gel purified using QiaexII reagents (Qiagen) according to the manufacturer's protocol.

Sequence analysis was performed and ZC16,795 (SEQ ID NO:9) was designed to be used in a PCR reaction with ZC15,255 (SEQ ID NO:10) using the skeletal muscle cDNA described above. PCR conditions were as follows: one cycle at 94° C. for 2'; 4 cycles at 94° C. for 20', and 72° C. for 3'; 4 cycles at 94° C. for 20", and 68° C. for 3; 25 cycles at 94° C. for 20", 66° C. for 20", 72° C. for 3', one cycle at 72° C. for 5'; followed by 4° C. hold. The reaction was electrophoresed on a 1.5% agarose gel and a 1.4kb band was excised and gel purified using QiaexII reagents and protocol (Qiagen).

Sequence analysis was performed and confirmed 5' extension of the initial EST sequence. This information was used to mine an EST database a second time. A second EST sequence was identified and contained in a plasmid. Confirmation of the second EST sequence was made by sequence analyses of the cDNA from which the EST originated. The clone appeared to have the complete 5' end of zapop3.

The sequencing reactions described above used the following primers in a standard sequencing protocol: ZC447 (SEQ ID NO:1), ZC976 (SEQ ID NO:12), ZC18,222 (SEQ ID NO:13), ZC18,228 (SEQ ID NO:14), ZC18,283 (SEQ ID NO:15), and ZC18,284 (SEQ ID NO:16), ZC694 (SEQ ID NO:17), ZC6,768 (SEQ ID NO:18), ZC16,257 (SEQ ID NO:6), ZC15393 (SEQ ID NO:19), ZC15254 (SEQ ID NO:20), ZC15255 (SEQ ID NO:10), ZC15392 (SEQ ID NO:21).

Example 2

Tissue Distribution

Northern blot analysis was performed using Human Multiple Tissue Northern™ Blots (MTN I, MTN II, and MTN III) (Clontech). A 400 bp DNA fragment was excised from the plasmid containing the initial EST in Example 1, using ApaI (NEB). The fragment was purified using a commercially available kit (QiaexII™; Qiagen) and then radioactively labeled with $^{32}$P-dCTP using Rediprime™, a random prime labeling system (Amersham), according to the manufacturer's specifications. The probe was then purified using a Nuc-Trap™ column (Stratagene) according to the manufacturer's instructions. ExpressHyb™ (Clontech) solution was used for prehybridization and as a hybridizing solution for the Northern blots. Hybridization took place overnight at 55° C. using 2×10$^6$ cpm/ml of labeled probe. The blots were then washed in 2×SSC/1% SDS at room temperature and then 65° C., followed by a wash in 0.1×SSC/0.1% SDS at 65° C. A transcript was detected at approximately 2 kb with strong signals in heart and skeletal muscle. Moderate to weak signals were seen in most other tissues analyzed. No signals were apparent in ovary or lung tissues represented on the blots.

Dot Blots were also performed using Human RNA Master Blots™ (Clontech). The methods and conditions for the Dot Blots are the same as for the Multiple Tissue Blots disclosed above. Strong signal intensity was present in heart. A moderate signal was present in most other tissues analyzed. No signals were apparent in ovary or lung tissues represented on the blots.

Example 3

Chromosomal Assignment and Placement of Zapop3

Zapop3 was mapped to chromosome 9 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Zapop3 with the "GeneBridge 4 RH Panel", 20 µl reactions were set up in a 96-well microtiter plate (Stratagene, La Jolla, Calif.) and used in a "RoboCycler Gradient 96" thermal cycler (Stratagene). Each of the 95 PCR reactions consisted of 2 µl 10×KlenTaq PCR reaction buffer (Clontech Laboratories, Inc., Palo Alto, Calif.), 1.6 µl dNTPs mix (2.5 mM each, Perkin-Elmer, Foster City, Calif.), 1 µl sense primer, ZC 15,678 (SEQ ID NO:22), 1 µl antisense primer, ZC 15,679, (SEQ ID NO:23), 2 µl "Redi-Load" (Research Genetics, Inc., Huntsville, Ala.), 0.4 µl 50×Advantage KlenTaq Polymerase Mix (Clontech), 25 ng of DNA from an individual hybrid clone or control and ddH20 for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 66° C. and 1.5 minute extension at 72° C., followed by a final 1 cycle extension of 7 minutes at 72° C. The reactions were separated by electrophoresis on a 2% agarose gel (Life Technologies).

The results showed that Zapop3 maps 0.80 cR_3000 from the framework marker WI-6352 on the chromosome 9 WICGR radiation hybrid map. Proximal and distal framework markers were WI-6352 (D9S1144) and WI-9685 (D9S 1721), respectively. The use of surrounding markers positions Zapop3 in the 9q34.11 region on the integrated LDB chromosome 9 map (The Genetic Location Database, University of Southhampton, WWW server: http://cedar.genetics.soton.ac.uk/public_html/).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An expression vector comprising the following operably linked elements:

a transcription promoter;

a DNA segment encoding a polypeptide having an amino acid sequence as shown in SEQ ID NO:2 from amino acid number 1 (Met), to amino acid number 723 (Ser); and a transcription terminator, wherein the promoter is operably linked to the DNA segment, and the DNA segment is operably linked to the transcription terminator.

2. An expression vector according to claim 1, further comprising a secretory signal sequence operably linked to the DNA segment.

3. A cultured cell into which has been introduced an expression vector according to claim 1, wherein the cell expresses the polypeptide encoded by the DNA segment.

4. A method of producing a polypeptide comprising SEQ ID NO:2 comprising:

culturing a cell according to claim 3, and isolating the zapop3 polypeptide produced by the cell.

* * * * *

SEQUENCE LISTING

<160> NUMBER OF SEQ ID NOS: 23

<210> SEQ ID NO 1
<211> LENGTH: 3138
<212> TYPE: DNA
<213> ORGANISM: Homo sapiens
<220> FEATURE:
<221> NAME/KEY: CDS
<222> LOCATION: (367)...(2535)

<400> SEQUENCE: 1

```
ccagtaccgc ggcgacccct gctccctcga gcacttgttg tgtgcacttt agttatcaaa      60
acagtctatg tggaaatcca gtcccgctct tcattcggag agtccgcgat tcctagagcc     120
tcagacttcg tcatcccggt ctgcgtgact ttatgagatt ctgagtttct gttcccagca     180
cctgcctttg aaggagacca gactccggct ccgcccggcc cgtgccgggt ggtctgcggc     240
cccgagtccg tgaccaagcc ctccgagtga tcggcctgcc ctcgggtgca cccgcgggtc     300
ccaacgtggg ggatccctcc atccgcaaag ccagggtcct aaagatcgct ctgggaaaag     360 ggaagg atg ccg ctc ttc ttc cgg aag cgg aaa ccc agt gag gag gct         408
       Met Pro Leu Phe Phe Arg Lys Arg Lys Pro Ser Glu Glu Ala
        1               5                  10 cgg aaa cgc ctg gag tac cag atg tgt ttg gca aaa gaa gct ggg gca        456
Arg Lys Arg Leu Glu Tyr Gln Met Cys Leu Ala Lys Glu Ala Gly Ala
 15              20                  25                  30 gat gac att ctc gac atc tct aaa tgt gag ctc tca gag att cca ttt        504
Asp Asp Ile Leu Asp Ile Ser Lys Cys Glu Leu Ser Glu Ile Pro Phe
             35                  40                  45 gga gct ttt gca aca tgc aaa gtt ctg cag aag aag gtg ctg atc gtc        552
Gly Ala Phe Ala Thr Cys Lys Val Leu Gln Lys Lys Val Leu Ile Val
         50                  55                  60 cac acg aat cac ctc act tcc ctg ctt ccc aaa tcc tgc agc ctc ctg        600
His Thr Asn His Leu Thr Ser Leu Leu Pro Lys Ser Cys Ser Leu Leu
     65                  70                  75 agt ctg gca acc att aag gtt cta gat ctc cac gat aat cag ctg aca        648
Ser Leu Ala Thr Ile Lys Val Leu Asp Leu His Asp Asn Gln Leu Thr
 80                  85                  90 gcc ctt cct gac gat ctg ggg cag ctg act gcc ctc cag gtc tta aac        696
Ala Leu Pro Asp Asp Leu Gly Gln Leu Thr Ala Leu Gln Val Leu Asn
 95                 100                 105                 110 gtg gaa agg aat caa ctg atg cag ctc cca cgt tcc att ggg aac ctg        744
Val Glu Arg Asn Gln Leu Met Gln Leu Pro Arg Ser Ile Gly Asn Leu
             115                 120                 125 acc cag ctc cag act ctc aat gtt aaa gac aac aag ctg aag gag ctt        792
Thr Gln Leu Gln Thr Leu Asn Val Lys Asp Asn Lys Leu Lys Glu Leu
         130                 135                 140 cca gac acc gtg ggg gag ctt cga agc ctg cgt acc ctc aac atc agt        840
Pro Asp Thr Val Gly Glu Leu Arg Ser Leu Arg Thr Leu Asn Ile Ser
     145                 150                 155 gga aac gag atc cag aga ttg ccg cag atg ctg gct cac gtt cga acc        888
Gly Asn Glu Ile Gln Arg Leu Pro Gln Met Leu Ala His Val Arg Thr
 160                 165                 170 ctg gag atg ctg agc ctt gac gcc tcg gcc atg gtc tac ccg ccg cgg        936
Leu Glu Met Leu Ser Leu Asp Ala Ser Ala Met Val Tyr Pro Pro Arg
175                 180                 185                 190 gag gtg tgt ggt gcc ggc act gcg gcc atc ttg cag ttc ctc tgc aaa        984
Glu Val Cys Gly Ala Gly Thr Ala Ala Ile Leu Gln Phe Leu Cys Lys
             195                 200                 205
```

-continued

| | |
|---|---|
| gag tca ggg ctg gaa tac tac ccc cct tct cag tac ttg ctg cca att<br>Glu Ser Gly Leu Glu Tyr Tyr Pro Pro Ser Gln Tyr Leu Leu Pro Ile<br>210 215 220 | 1032 |
| ctg gag caa gat gga atc gag aac tct cgg gac agc cct gat ggg ccc<br>Leu Glu Gln Asp Gly Ile Glu Asn Ser Arg Asp Ser Pro Asp Gly Pro<br>225 230 235 | 1080 |
| acg gac aga ttc tca agg gag gag tta gag tgg cag aac agg ttc tca<br>Thr Asp Arg Phe Ser Arg Glu Glu Leu Glu Trp Gln Asn Arg Phe Ser<br>240 245 250 | 1128 |
| gac tat gag aag agg aag gaa cag aag atg ctg gag aaa ctc gag ttt<br>Asp Tyr Glu Lys Arg Lys Glu Gln Lys Met Leu Glu Lys Leu Glu Phe<br>255 260 265 270 | 1176 |
| gaa cgg cgc ctg gaa ctg ggg cag cgg gag cac acc cag ctc ctt cag<br>Glu Arg Arg Leu Glu Leu Gly Gln Arg Glu His Thr Gln Leu Leu Gln<br>275 280 285 | 1224 |
| cag agc agc agc cag aag gat gag atc ctt cag acg gtc aag gag gag<br>Gln Ser Ser Ser Gln Lys Asp Glu Ile Leu Gln Thr Val Lys Glu Glu<br>290 295 300 | 1272 |
| cag tcc cgg ctg gag cag ggc ctg agt gag cac cag cgc cac ctc gac<br>Gln Ser Arg Leu Glu Gln Gly Leu Ser Glu His Gln Arg His Leu Asp<br>305 310 315 | 1320 |
| gca gag cgg cag cgg ctg cag gag cag ctg aag cag acg gaa cag aac<br>Ala Glu Arg Gln Arg Leu Gln Glu Gln Leu Lys Gln Thr Glu Gln Asn<br>320 325 330 | 1368 |
| att tcc agc cgg atc cag aag ctg ctg cag gac aat cag aga caa aag<br>Ile Ser Ser Arg Ile Gln Lys Leu Leu Gln Asp Asn Gln Arg Gln Lys<br>335 340 345 350 | 1416 |
| aaa agc tcc gag att ttg aaa tcg ctg gaa aat gaa aga ata aga atg<br>Lys Ser Ser Glu Ile Leu Lys Ser Leu Glu Asn Glu Arg Ile Arg Met<br>355 360 365 | 1464 |
| gaa cag ttg atg tcc ata acc cag gag gag act gag agc ctg cgg cga<br>Glu Gln Leu Met Ser Ile Thr Gln Glu Glu Thr Glu Ser Leu Arg Arg<br>370 375 380 | 1512 |
| cgt gac gtt gcc tcc gcc atg cag cag atg ctg act gag agc tgt aag<br>Arg Asp Val Ala Ser Ala Met Gln Gln Met Leu Thr Glu Ser Cys Lys<br>385 390 395 | 1560 |
| aac cgg ctc atc cag atg gcc tac gaa tct cag agg cag aac ttg gtc<br>Asn Arg Leu Ile Gln Met Ala Tyr Glu Ser Gln Arg Gln Asn Leu Val<br>400 405 410 | 1608 |
| cag cag gcc tgt tcc agc atg gcc gaa atg gat gaa cga ttc cag cag<br>Gln Gln Ala Cys Ser Ser Met Ala Glu Met Asp Glu Arg Phe Gln Gln<br>415 420 425 430 | 1656 |
| att ctg tcg tgc cag caa atg gat cag aac aaa gcc atc agc cag atc<br>Ile Leu Ser Cys Gln Gln Met Asp Gln Asn Lys Ala Ile Ser Gln Ile<br>435 440 445 | 1704 |
| ctg cag gag agc gcg atg cag aag gct gcg ttc gag gca ctc cag gtg<br>Leu Gln Glu Ser Ala Met Gln Lys Ala Ala Phe Glu Ala Leu Gln Val<br>450 455 460 | 1752 |
| aag aaa gac ctg atg cat cgg cag atc agg agc cag att aag tta ata<br>Lys Lys Asp Leu Met His Arg Gln Ile Arg Ser Gln Ile Lys Leu Ile<br>465 470 475 | 1800 |
| gaa act gag tta ttg cag ctg aca cag ctg gag tta aag agg aag tcc<br>Glu Thr Glu Leu Leu Gln Leu Thr Gln Leu Glu Leu Lys Arg Lys Ser<br>480 485 490 | 1848 |
| ctg gac aca gag tca ctc cag gag atg atc tcg gag cag cgc tgg gcc<br>Leu Asp Thr Glu Ser Leu Gln Glu Met Ile Ser Glu Gln Arg Trp Ala<br>495 500 505 510 | 1896 |
| ctc agc tcc ctg ctc cag cag ctg ctc aaa gag aag cag cag cga gag<br>Leu Ser Ser Leu Leu Gln Gln Leu Leu Lys Glu Lys Gln Gln Arg Glu<br>515 520 525 | 1944 |

```
gaa gag ctc cgg gaa atc ctg acg gag tta gaa gcc aaa agt gaa acc      1992
Glu Glu Leu Arg Glu Ile Leu Thr Glu Leu Glu Ala Lys Ser Glu Thr
            530                 535                 540 agg cag gaa aat tac tgg ctg att cag tat caa cgg ctt ttg aac cag      2040
Arg Gln Glu Asn Tyr Trp Leu Ile Gln Tyr Gln Arg Leu Leu Asn Gln
        545                 550                 555 aag ccc ttg tcc ttg aag ctg caa gaa gag ggg atg gag cgc cag ctg      2088
Lys Pro Leu Ser Leu Lys Leu Gln Glu Glu Gly Met Glu Arg Gln Leu
    560                 565                 570 gtg gcc ctc ctg gag gag ctg tcg gct gag cac tac ctg ccc atc ttt      2136
Val Ala Leu Leu Glu Glu Leu Ser Ala Glu His Tyr Leu Pro Ile Phe
575                 580                 585                 590 gcg cac cac cgc ctc tca ctg gac ctg ctg agc caa atg agc cca ggg      2184
Ala His His Arg Leu Ser Leu Asp Leu Leu Ser Gln Met Ser Pro Gly
                595                 600                 605 gac ctg gcc aag gtg ggc gtc tca gaa gct ggc ctg cag cac gag atc      2232
Asp Leu Ala Lys Val Gly Val Ser Glu Ala Gly Leu Gln His Glu Ile
            610                 615                 620 ctc cgg aga gtc cag gaa ctg ctg gat gca gcc agg atc cag cca gag      2280
Leu Arg Arg Val Gln Glu Leu Leu Asp Ala Ala Arg Ile Gln Pro Glu
        625                 630                 635 ctg aaa cca cca atg ggt gag gtc gtc acc cct acg gcc ccc cag gag      2328
Leu Lys Pro Pro Met Gly Glu Val Val Thr Pro Thr Ala Pro Gln Glu
    640                 645                 650 cct cct gag tct gtg agg cca tcc gct ccc cct gca gag ctg gag gtg      2376
Pro Pro Glu Ser Val Arg Pro Ser Ala Pro Ala Glu Leu Glu Val
655                 660                 665                 670 cag gcc tca gag tgt gtc gtg tgc ctg gaa cgg gag gcc cag atg atc      2424
Gln Ala Ser Glu Cys Val Val Cys Leu Glu Arg Glu Ala Gln Met Ile
                675                 680                 685 ttc ctc aac tgt ggc cac gtc tgc tgc tgc cag cag tgc tgc cag cca      2472
Phe Leu Asn Cys Gly His Val Cys Cys Cys Gln Gln Cys Cys Gln Pro
            690                 695                 700 ctg cgc acc tgc ccg ctg tgc cgc cag gac atc gcc cag cgc ctc cgc      2520
Leu Arg Thr Cys Pro Leu Cys Arg Gln Asp Ile Ala Gln Arg Leu Arg
        705                 710                 715 atc tac cac agc agc tgagtgctgc ccgcccacct gggcctggtc ctagccctgc      2575
Ile Tyr His Ser Ser
    720 ctcggccact gtgagcccg ggctcctgct cagccttgtg ccagccagac tcgtatgagg     2635 ctccccctg ccctgggccc cttccccact gccaggagc cccatccta agctccaagc       2695 atgtctgggc caggcagagg tgctcctcat ccatgacacc accagtctga atggtcctgg    2755 gggctggggc tggagaggcc gctgcaccac cacccgagct gggagccag cgtcccagcc     2815 taatcacgga tctgctgcct cccagctgtc ttgactgaag gccaccgccc ctgcaggagc    2875 ttgggtcctc atctggggc catgcacagg cccgtcccac cctgcatgtg ggaagggagc     2935 aggagggcct ggctgggtga ggggaggcct tcctgggaag gcgtgtggtg caggcctgtg    2995 ctcacagtgg caccagcaac cctgggtctc cctctctgct gctccccaga accccggggc    3055 cctcctgctc tccacaactg tccctcctta ccccatgtag ctcgatccga agcaggagtg    3115 tcaataaaacc tgtcttcagt gca                                           3138

<210> SEQ ID NO 2
<211> LENGTH: 723
<212> TYPE: PRT
<213> ORGANISM: Homo sapiens
```

-continued

<400> SEQUENCE: 2

```
Met Pro Leu Phe Phe Arg Lys Arg Lys Pro Ser Glu Glu Ala Arg Lys
 1               5                  10                  15

Arg Leu Glu Tyr Gln Met Cys Leu Ala Lys Glu Ala Gly Ala Asp Asp
                20                  25                  30

Ile Leu Asp Ile Ser Lys Cys Glu Leu Ser Glu Ile Pro Phe Gly Ala
                35                  40                  45

Phe Ala Thr Cys Lys Val Leu Gln Lys Val Leu Ile Val His Thr
 50                  55                  60

Asn His Leu Thr Ser Leu Leu Pro Lys Ser Cys Ser Leu Leu Ser Leu
 65                  70                  75                  80

Ala Thr Ile Lys Val Leu Asp Leu His Asp Asn Gln Leu Thr Ala Leu
                85                  90                  95

Pro Asp Asp Leu Gly Gln Leu Thr Ala Leu Gln Val Leu Asn Val Glu
                100                 105                 110

Arg Asn Gln Leu Met Gln Leu Pro Arg Ser Ile Gly Asn Leu Thr Gln
                115                 120                 125

Leu Gln Thr Leu Asn Val Lys Asp Asn Lys Leu Lys Glu Leu Pro Asp
    130                 135                 140

Thr Val Gly Glu Leu Arg Ser Leu Arg Thr Leu Asn Ile Ser Gly Asn
145                 150                 155                 160

Glu Ile Gln Arg Leu Pro Gln Met Leu Ala His Val Arg Thr Leu Glu
                165                 170                 175

Met Leu Ser Leu Asp Ala Ser Ala Met Val Tyr Pro Pro Arg Glu Val
                180                 185                 190

Cys Gly Ala Gly Thr Ala Ala Ile Leu Gln Phe Leu Cys Lys Glu Ser
                195                 200                 205

Gly Leu Glu Tyr Tyr Pro Pro Ser Gln Tyr Leu Leu Pro Ile Leu Glu
                210                 215                 220

Gln Asp Gly Ile Glu Asn Ser Arg Asp Ser Pro Asp Gly Pro Thr Asp
225                 230                 235                 240

Arg Phe Ser Arg Glu Glu Leu Glu Trp Gln Asn Arg Phe Ser Asp Tyr
                245                 250                 255

Glu Lys Arg Lys Glu Gln Lys Met Leu Glu Lys Leu Glu Phe Glu Arg
                260                 265                 270

Arg Leu Glu Leu Gly Gln Arg Glu His Thr Gln Leu Leu Gln Gln Ser
                275                 280                 285

Ser Ser Gln Lys Asp Glu Ile Leu Gln Thr Val Lys Glu Glu Gln Ser
    290                 295                 300

Arg Leu Glu Gln Gly Leu Ser Glu His Gln Arg His Leu Asp Ala Glu
305                 310                 315                 320

Arg Gln Arg Leu Gln Glu Gln Leu Lys Gln Thr Glu Gln Asn Ile Ser
                325                 330                 335

Ser Arg Ile Gln Lys Leu Leu Gln Asp Asn Gln Arg Gln Lys Lys Ser
                340                 345                 350

Ser Glu Ile Leu Lys Ser Leu Glu Asn Glu Arg Ile Arg Met Glu Gln
                355                 360                 365

Leu Met Ser Ile Thr Gln Glu Glu Thr Glu Ser Leu Arg Arg Arg Asp
    370                 375                 380

Val Ala Ser Ala Met Gln Gln Met Leu Thr Glu Ser Cys Lys Asn Arg
385                 390                 395                 400

Leu Ile Gln Met Ala Tyr Glu Ser Gln Arg Gln Asn Leu Val Gln Gln
                405                 410                 415
```

```
Ala Cys Ser Ser Met Ala Glu Met Asp Glu Arg Phe Gln Gln Ile Leu
            420                 425                 430

Ser Cys Gln Gln Met Asp Gln Asn Lys Ala Ile Ser Gln Ile Leu Gln
        435                 440                 445

Glu Ser Ala Met Gln Lys Ala Ala Phe Glu Ala Leu Gln Val Lys Lys
    450                 455                 460

Asp Leu Met His Arg Gln Ile Arg Ser Gln Ile Lys Leu Ile Glu Thr
465                 470                 475                 480

Glu Leu Leu Gln Leu Thr Gln Leu Glu Leu Lys Arg Lys Ser Leu Asp
                485                 490                 495

Thr Glu Ser Leu Gln Glu Met Ile Ser Glu Gln Arg Trp Ala Leu Ser
            500                 505                 510

Ser Leu Leu Gln Gln Leu Leu Lys Glu Lys Gln Gln Arg Glu Glu Glu
        515                 520                 525

Leu Arg Glu Ile Leu Thr Glu Leu Glu Ala Lys Ser Glu Thr Arg Gln
    530                 535                 540

Glu Asn Tyr Trp Leu Ile Gln Tyr Gln Arg Leu Leu Asn Gln Lys Pro
545                 550                 555                 560

Leu Ser Leu Lys Leu Gln Glu Glu Gly Met Glu Arg Gln Leu Val Ala
                565                 570                 575

Leu Leu Glu Glu Leu Ser Ala Glu His Tyr Leu Pro Ile Phe Ala His
            580                 585                 590

His Arg Leu Ser Leu Asp Leu Leu Ser Gln Met Ser Pro Gly Asp Leu
        595                 600                 605

Ala Lys Val Gly Val Ser Glu Ala Gly Leu Gln His Glu Ile Leu Arg
    610                 615                 620

Arg Val Gln Glu Leu Leu Asp Ala Ala Arg Ile Gln Pro Glu Leu Lys
625                 630                 635                 640

Pro Pro Met Gly Glu Val Val Thr Pro Thr Ala Pro Gln Glu Pro Pro
                645                 650                 655

Glu Ser Val Arg Pro Ser Ala Pro Ala Glu Leu Glu Val Gln Ala
            660                 665                 670

Ser Glu Cys Val Val Cys Leu Glu Arg Glu Ala Gln Met Ile Phe Leu
        675                 680                 685

Asn Cys Gly His Val Cys Cys Gln Gln Cys Cys Gln Pro Leu Arg
    690                 695                 700

Thr Cys Pro Leu Cys Arg Gln Asp Ile Ala Gln Arg Leu Arg Ile Tyr
705                 710                 715                 720

His Ser Ser

<210> SEQ ID NO 3
<211> LENGTH: 2169
<212> TYPE: DNA
<213> ORGANISM: Artificial Sequence
<220> FEATURE:
<223> OTHER INFORMATION: Degenerate polynucleotide sequence of zapop3
<220> FEATURE:
<221> NAME/KEY: misc_feature
<222> LOCATION: (1)...(2169)
<223> OTHER INFORMATION: n = A,T,C or G

<400> SEQUENCE: 3
atgccnytnt tyttymgnaa rmgnaarccn wsngargarg cnmgnaarmg nytngartay      60
caratgtgyy tngcnaarga rgcnggngcn gaygayathy tngayathws naartgygar    120
ytnwsngara thccnttygg ngcnttygcn acntgyaarg tnytncaraa raargtnytn    180
```

```
athgtncaya cnaaycayyt nacnwsnytn ytnccnaarw sntgywsnyt nytnwsnytn      240
gcnacnatha argtnytnga yytncaygay aaycarytna cngcnytncc ngaygayytn      300
ggncarytna cngcnytnca rgtnytnaay gtngarmgna aycarytnat gcarytnccn      360
mgnwsnathg gnaayytnac ncarytncar acnytnaayg tnaargayaa yaarytnaar     420
garytnccng ayacngtngg ngarytnmgn wsnytnmgna cnytnaayat hwsnggnaay      480
garathcarm gnytnccnca ratgytngcn caygtnmgna cnytngarat gytnwsnytn      540
gaygcnwsng cnatggtnta yccncnmgn gargtntgyg gngcnggnac ngcngcnath       600
ytncarttyy tntgyaarga rwsnggnytn gartaytayc cnccnwsnca rtayytnytn     660
ccnathytng arcargaygg nathgaraay wsnmgngayw snccngaygg nccnacngay      720
mgnttywsnm gngargaryt ngartggcar aaymgnttyw sngaytayga raarmgnaar     780
garcaraara tgytngaraa rytngartty garmgnmgny tngarytngg ncarmgngar      840
cayacncary tnytncarca rwsnwsnwsn caraargayg arathytnca racngtnaar     900
gargarcarw snmgnytnga rcarggnytn wsngarcayc armgncayyt ngaygcngar     960
mgncarmgny tncargarca rytnaarcar acngarcara ayathwsnws nmgnathcar     1020
aarytnytnc argayaayca rmgncaraar aarwsnwsng arathytnaa rwsnytngar     1080
aaygarmgna thmgnatgga rcarytnatg wsnathacnc argargarac ngarwsnytn     1140
mgnmgnmgng aygtngcnws ngcnatgcar caratgytna cngarwsntg yaaraaymgn     1200
ytnathcara tggcntayga rwsncarmgn caraayytng tncarcargc ntgywsnwsn     1260
atggcngara tggaygarmg nttycarcar athytnwsnt gycarcarat ggaycaraay     1320
aargcnathw sncarathyt ncargarwsn gcnatgcara argcngcntt ygargcnytn     1380
cargtnaara argayytnat gcaymgncar athmgnwsnc arathaaryt nathgaracn     1440
garytnytnc arytnacnca rytngarytn aarmgnaarw snytngayac ngarwsnytn     1500
cargaratga thwsngarca rmgntgggcn ytnwsnwsny tnytncarca rytnytnaar     1560
garaarcarc armgngarga rgarytnmgn garathytna cngarytnga rgcnaarwsn     1620
garacnmgnc argaraayta ytggytnath cartaycarm gnytnytnaa ycaraarccn     1680
ytnwsnytna arytncarga rgarggnatg garmgncary tngtngcnyt nytngargar     1740
ytnwsngcng arcaytayyt nccnathtty gcncaycaym gnytnwsnyt ngayytnytn     1800
wsncaratgw snccnggnga yytngcnaar gtnggngtnw sngargcngg nytncarcay     1860
garathytnm gnmgngtnca rgarytnytn gaygcngcnm gnathcarcc ngarytnaar     1920
ccnccnatgg gngargtngt nacnccnacn gcnccncarg arccnccnga rwsngtnmgn     1980
ccnwsngcnc cnccngcnga rytngargtn cargcnwsng artgygtngt ntgyytngar     2040
mgngargcnc aratgathtt yytnaaytgy ggncaygtnt gytgytgyca rcartgytgy     2100
carccnytnm gnacntgycc nytntgymgn cargayathg cncarmgnyt nmgnathtay     2160 caywsnwsn                                                              2169
```

<210> SEQ ID NO 4
<211> LENGTH: 8
<212> TYPE: PRT
<213> ORGANISM: Artificial Sequence
<220> FEATURE:
<223> OTHER INFORMATION: Flag peptide sequence

<400> SEQUENCE: 4

Asp Tyr Lys Asp Asp Asp Asp Lys
 1               5

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide primer ZC9739

<400> SEQUENCE: 5
ccatcctaat acgactcact atagggc                                      27

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer ZC16257

<400> SEQUENCE: 6
tttgctgcca cgacagaatc tg                                           22

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer ZC9719

<400> SEQUENCE: 7
actcactata gggctcgagc ggc                                          23

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer ZC16568

<400> SEQUENCE: 8
ggaatcgttc atccatttcg                                              20

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide primer ZC16795

<400> SEQUENCE: 9
taacccagga ggagactgag ag                                           22

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer ZC15255

<400> SEQUENCE: 10
ccccagcccc caggaccatt                                              20

```
<210> SEQ ID NO 11
<211> LENGTH: 17
<212> TYPE: DNA
<213> ORGANISM: Artificial Sequence
<220> FEATURE:
<223> OTHER INFORMATION: Oligonucleotide primer ZC447

<400> SEQUENCE: 11
taacaatttc acacagg                                                   17

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 12
cgttgtaaaa cgacggcc                                                  18

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide Primer ZC18222

<400> SEQUENCE: 13
actctaactc ctcccttgag                                                20

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer ZC18228

<400> SEQUENCE: 14
atgccgctct tcttccggaa g                                              21

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide Primer ZC18283

<400> SEQUENCE: 15
agctgcatca gttgattcc                                                 19

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide Primer ZC18284

<400> SEQUENCE: 16
aaggagcttc cagacaccg                                                 19

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer ZC694
```

-continued

```
<400> SEQUENCE: 17
taatacgact cactataggg                                              20

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide primer ZC6768

<400> SEQUENCE: 18
gcaattaacc ctcactaaag ggaac                                        25

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer ZC15393

<400> SEQUENCE: 19
ggatggcctc acagactcag                                              20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer ZC15254

<400> SEQUENCE: 20
gcctctcact ggacctgctg                                              20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer ZC15392

<400> SEQUENCE: 21
tgccagccag actcgtatga                                              20

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide Primer ZC15678

<400> SEQUENCE: 22
cgcctccgca tctaccac                                                18

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide Primer ZC15679

<400> SEQUENCE: 23
taatacgact cactataggg                                              20
```